US008608310B2

(12) United States Patent
Otis et al.

(10) Patent No.: US 8,608,310 B2
(45) Date of Patent: Dec. 17, 2013

(54) WIRELESS POWERED CONTACT LENS WITH BIOSENSOR

(75) Inventors: Brian Otis, Seattle, WA (US); Yu-Te Liao, Taichung (TW); Babak Amirparviz, Mountain View, CA (US); Huanfen Yao, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 77 days.

(21) Appl. No.: 13/401,569

(22) Filed: Feb. 21, 2012

(65) Prior Publication Data

US 2012/0245444 A1 Sep. 27, 2012

Related U.S. Application Data

(63) Continuation-in-part of application No. 13/278,026, filed on Oct. 20, 2011, which is a continuation-in-part of application No. 12/742,081, filed as application No. PCT/US2008/082827 on Nov. 7, 2008, now Pat. No. 8,394,660.

(60) Provisional application No. 61/444,257, filed on Feb. 18, 2011, provisional application No. 61/394,977, filed on Oct. 20, 2010, provisional application No. 60/986,197, filed on Nov. 7, 2007.

(51) Int. Cl.
*G02C 7/04* (2006.01)
*A61B 3/00* (2006.01)
*A61B 5/00* (2006.01)

(52) U.S. Cl.
USPC ............... 351/159.03; 351/219; 600/319

(58) Field of Classification Search
USPC ............... 351/159.03, 159.39, 219; 600/319
See application file for complete search history.

(56) References Cited

U.S. PATENT DOCUMENTS

| 8,096,654 B2 * | 1/2012 | Amirparviz et al. ........ 351/159.4 |
| 8,446,341 B2 * | 5/2013 | Amirparviz et al. ............. 345/7 |
| 2012/0201755 A1 * | 8/2012 | Rozakis et al. ................ 424/9.1 |
| 2013/0135578 A1 * | 5/2013 | Pugh et al. ............... 351/159.39 |

OTHER PUBLICATIONS

Ahmadi, M.M., and G.A. Jullien, "Current-Mirror-Based Potentiostats for Three-Electrode Amperometric Electrochemical Sensors," IEEE Transactions on Circuits and Systems—I: Regular Papers 56(7):1339-1348, Jul. 2009.
Ahmadi, M.M., and G.A. Jullien, "A Wireless-Implantable Microsystem for Continuous Blood Glucose Monitoring," IEEE Transactions on Biomedical Circuits and Systems 3(3):169-180, Jun. 2009.

(Continued)

*Primary Examiner* — Jordan Schwartz
(74) *Attorney, Agent, or Firm* — Christensen O'Connor Johnson Kindness PLLC

(57) ABSTRACT

A contact lens having an integrated glucose sensor is provided. The contact lens includes an electrochemical sensor configured to measure the level of glucose in the tear fluid of the eye of the user wearing the contact lens. The electrochemical sensor is powered by radiation off-lens, through an RF antenna or a photovoltaic device mounted on the periphery of the contact lens. The power provided to the contact lens also enables transmission of data from the electrochemical sensor, for example by backscatter communications or optically by an LED mounted to the lens.

11 Claims, 28 Drawing Sheets

(56) References Cited

OTHER PUBLICATIONS

Chu, M.X., et al., "Soft Contact Lens Biosensor for In Situ Monitoring of Tear Glucose as Non-Invasive Blood Sugar Assessment," Talanta 83(3):960-965, Jan. 2011.

Haider, M.R., et al., "Low-Power Low-Voltage Current Readout Circuit for Inductively Powered Implant System," IEEE Transactions on Biomedical Circuits and Systems 4(4):205-213, Aug. 2010.

Pandey, J., et al., "A Fully Integrated RF-Powered Contact Lens With a Single Element Display," IEEE Transactions on Biomedical Circuits and Systems 4(6):454-461, Dec. 2010.

Yao, H., et al., "A Dual Microscale Glucose Sensor on a Contact Lens, Tested in Conditions Mimicking the Eye," IEEE 24th International Conference on Micro Electro Mechanical Systems (MEMS), Cancun, Mexico, Jan. 23-27, 2011, pp. 25-28.

Yeager, D., et al., "A 9 µA, Addressable Gen2 Sensor Tag for Biosignal Acquisition," IEEE Journal of Solid-State Circuits 45(10):2198-2209, Oct. 2010.

\* cited by examiner

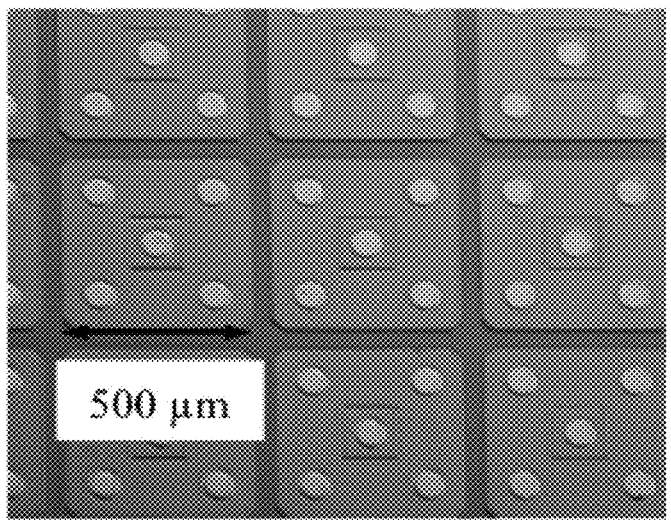
*Fig.8A.*
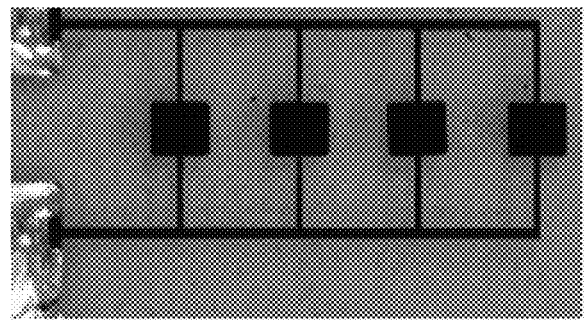
*Fig.8C.*
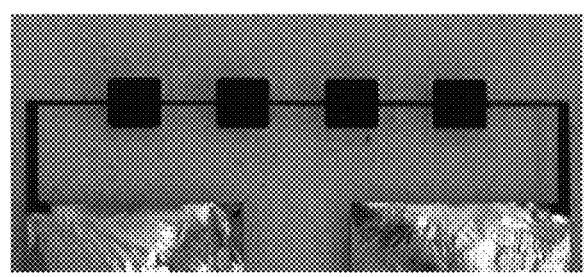
*Fig.8B.*
*Fig.8D.*

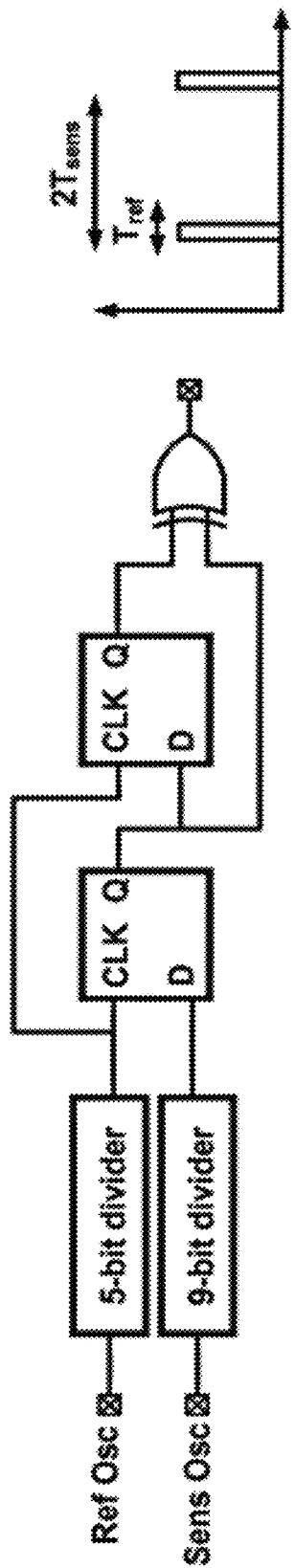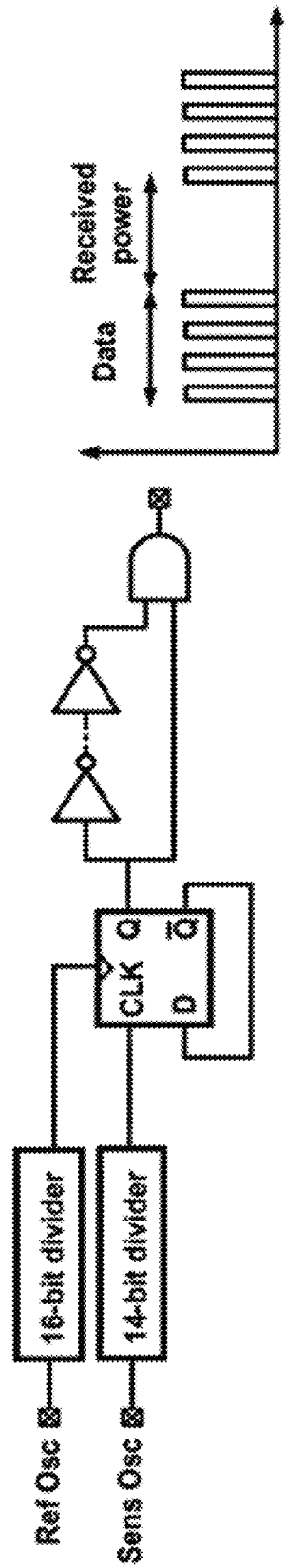
Fig. 26A.
Fig. 26B.

WIRELESS POWERED CONTACT LENS WITH BIOSENSOR

CROSS-REFERENCES TO RELATED APPLICATIONS

This application claims the benefit of U.S. Provisional Application No. 61/444,257, filed Feb. 18, 2011, and is a continuation-in-part of U.S. patent application Ser. No. 13/278,026, filed Oct. 20, 2011, which claims the benefit of U.S. Provisional Application No. 61/394,977, filed Oct. 20, 2010, and is a continuation-in-part of U.S. patent application Ser. No. 12/742,081, filed Sep. 15, 2010, which is the national stage of International Application No. PCT/US2008/082827, filed Nov. 7, 2008, which claims the benefit of U.S. Provisional Application No. 60/986,197, filed Nov. 7, 2007, all of the disclosures of which are hereby expressly incorporated by reference in their entirety.

STATEMENT OF GOVERNMENT LICENSE RIGHTS

This invention was made with government support under grant number 25969810-50204-A, awarded by the Defense Advanced Research Projects Agency of the Department of Defense, and grant number EFR0937710, awarded by the National Science Foundation. The government has certain rights in the invention.

BACKGROUND

Self-assembly has emerged as a powerful fabrication technology for fabricating macroelectronic devices. Macrofabrication technologies typically integrate a large number of various functional components over areas exceeding the size of a typical semiconductor wafer and do so in a cost-effective and time-efficient fashion. A typical self-assembly macrofabrication technique includes functional devices that are batch microfabricated (for example, on a semiconductor substrate) and released to yield a collection of free-standing components. These components are then allowed to self-assemble onto a template, for example, on a plastic substrate, to yield a functional macroelectronic system. Because self-assembly is an inherently parallel construction method, it allows for cost-effective and time-efficient integration of a large number of functional components onto both conventional (e.g., semiconductor) and unconventional (e.g., plastic) substrates.

An additional benefit of self-assembled macrofabrication is that it allows for the integration of components made from incompatible microfabrication processes (e.g., light-emitting diodes made in compound semiconductor substrates and silicon transistors) onto nonplanar and/or flexible substrates.

The components of a self-assembly based macroelectronic fabrication system typically include (1) the development of fabrication processes that generate free-standing functional components; (2) the implementation of recognition/binding capabilities to guide the components to bind in the correct location; and (3) the determination of self-assembly procedures/conditions that result in a final assembled system with a high yield of components in correct locations. An exemplary fluidic self-assembly method is disclosed in International Patent Application No. PCT/US2007/072038, filed Jun. 25, 2007, which is hereby incorporated by reference in its entirety. Additionally, fluidic self-assembly has been used to fabricate macro-scale electronics comprising an integrated optical analysis system in International Application No. PCT/US2008/050104, which is also hereby incorporated by reference in its entirety.

Briefly, the above-referenced international patent applications describe a method for self-assembly that accomplishes the assembly process in one step, obviating or mitigating the need for post-processing of an assembled macro-electronic device. Microcomponents are fabricated having a particular shape, and a template with embedded interconnects is fabricated having recessed binding sites that are sized to receive particular microcomponent types. The binding sites include a low melting point alloy for electrically connecting received microcomponents to the interconnect network. The template is placed in a liquid, and the microcomponents are introduced to the liquid such that the microcomponents flow or slide along the template propelled by gravity and/or fluid-dynamic forces and some of them are received into the binding sites, and retained by capillary forces. The liquid is heated before or after introduction of the microcomponents to melt the alloy. The fluid and/or template are then cooled to harden the alloy, binding the microcomponents.

Prior macro-scale self-assembly techniques have produced macroelectronic devices having structures such as light-emitting diodes, photosensors, and transistors, to name a few. One aspect of previous macroelectronic self-assembled devices is the limitation of fabrication to patterning features on one side of a device. In a typical fabrication procedure for components for macro-scale self-assembly, micron-scale devices are patterned on a substrate and then released for self-assembly.

Given traditional microelectronic fabrication techniques, it is not surprising that only one side of the micron scale devices can be patterned, because only the top side of a substrate is typically processed in microfabrication. This remains true when fabricating micron-scale devices for macroelectronic self-assembly in that only the top side of a device is typically patterned and processed to create the device structure. The eventual bottom side of the device is buried within (or adjacent to) the carrier substrate during processing, and the bottom of the device is only revealed once the devices are released from the carrier substrate, at which point the devices are individually articulated and batch processing of a plurality of such devices would be nearly impossible.

A processing technique enabling the patterning of both the top and bottom sides of micron-scale devices for fluidic self-assembly of macroelectronics would enable more complex devices (both on the micro and macro-scale) and increase the number of currently available types of device structures. By allowing more complex features to be integrated onto macroelectronic devices, the functions of such devices will potentially be improved, expanded, and enhanced.

Contact lenses may be one product that would benefit from the integration of micron-scale devices into macroelectronic systems. Contact lenses could become complex systems with circuitry, sensors, memory, and telecommunications used to track key biomarkers in tears or to show information to the wearer. Concentrations of molecules such as glucose, lactate, or cholesterol on the surface of the eye could be measured, stored, and then communicated to a handheld reader or a mobile phone. Contact lens sensors have been used to measure eye movement, corneal temperature, blood oxygen, tear glucose concentration, and intraocular pressure. However, few have employed electronic sensing and wireless data readout, and previous work demonstrated limited operating distances. A functional contact lens system requires a source of power. All prior work in this area has used either a wired approach to transfer power to the contact lens or has taken advantage of Radio Frequency (RF) power harvesting from a nearby source. The wired approach is helpful for validation of system components but cannot yield a stand-alone contact lens. RF power transmission requires an RF source in the vicinity of the contact lens and suffers from the low efficiency of small antennas that can fit within the form factor of a contact lens.

A supplemental power source (on lens) can increase the RF read range, as well as allow sensor sampling when RF power is not present.

Relatedly, miniaturized solar cells have been developed. For example, solar cells on 50 µm device-layer thickness silicon-on-insulator (SOI) wafers with isolation trenches etched to the buried oxide have been fabricated. The cells were connected in arrays with an estimated 14.3% efficiency at AM2.0. Similarly, another report used SOI wafers, isolation trenches, and arrays, but with device thicknesses of 5 and 10 µm. In both cases the cells remained on the handle wafer for mechanical stability and, hence, were not freestanding.

Diabetes is widely recognized as a leading cause of death and disability throughout the world, and the number of people diagnosed with diabetes mellitus is expected to increase dramatically in the next few decades. Diabetes management mainly concentrates on maintaining normal blood sugar levels through frequent glucose monitoring and the correct dosage and timing of insulin injections. Continuous glucose monitoring can help early diagnosis and effective control of diabetes complications.

An enzyme-based finger-pricking method is the most commonly used diabetic assessment. However, the procedure is invasive and inconvenient, requires patient compliance, and may cause infection during the blood sampling processes. An alternative method uses near-infrared spectroscopy and provides a noninvasive way to monitor the glucose level in the body. This method analyzes the light reflection or transmission spectrum in the fingertip to infer metabolic concentration. Due to challenges of interference with other biochemicals, poor signal strength, and calibration issues, this method is not sufficiently accurate for clinical use. Therefore, ongoing research focuses on the development of noninvasive and continuous glucose sensing.

Tear fluid is directly accessible on the eye and can be used as a chemical interface between a sensor and the human body. Tear fluid contains many biomarkers that are found in blood, such as glucose, cholesterol, sodium, and potassium. The glucose level in tear film is reported to be in the range of 0.1-0.6 millimoles per liter (mM), which is about ten times lower than the levels in blood.

Conventional contact lenses are transparent polymers placed on the eye to correct faulty vision and can simultaneously serve as a platform to directly access tear fluid. Integrating biosensors on a contact lens would provide a noninvasive way for continuously sensing metabolites in tear fluid. Contact-lens-mounted biosensors have been developed to measure eyelid pressure, tear glucose, and intraocular pressure. These sensors use inconvenient wired readout interfaces. Contact-lens functionality could be greatly expanded by creating heterogeneous systems with embedded electronics and wireless telemetry. Through integrating biological sensors and telemetry, an active contact lens could provide health professionals with a new tool for research studies and for diagnosing diseases without the need for lab chemistry or needles.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, a powered contact lens is provided. In one embodiment, the powered contact lens is formed from a transparent substrate shaped to be worn directly over a user's eye, the contact lens comprising:

(a) an annular antenna disposed at a margin of the contact lens, wherein the antenna is configured to both receive a power signal and transmit a data signal;

(b) a biosensor module configured to measure a characteristic of the user's eye, the biosensor module comprising and electrochemical sensor comprising:
    (i) a working electrode;
    (ii) a counter electrode;
    (iii) a reference electrode; and
    (iv) a biosensor circuit configured to measure the current across the working electrode and the counter electrode, to measure the voltage of the reference electrode, and to transmit a biosensor signal;
    wherein the working electrode, the counter electrode, and the reference electrode are all configured to be in electronic communication when the contact lens is worn on the user's eye; and (c) a communications module configured to:
    (i) process the power signal from the antenna to provide operational power to the biosensor module; and
    (ii) process the biosensor signal to provide the data signal to the antenna.

In another aspect, a powered contact lens is provided. In one embodiment, the powered contact lens is formed from a transparent substrate shaped to be worn directly over a user's eye, the contact lens comprising:

(a) an annular antenna disposed at a margin of the contact lens, wherein the antenna is configured to receive a power signal;

(b) a light-emitting diode (LED) configured to transmit a data signal;

(c) a biosensor module configured to measure a characteristic of the user's eye, the biosensor module comprising and electrochemical sensor comprising:
    (i) a working electrode;
    (ii) a counter electrode;
    (iii) a reference electrode; and
    (iv) a biosensor circuit configured to measure the voltage of the working electrode, the counter electrode, and the reference electrode, and to transmit a biosensor signal;
    wherein the working electrode, the counter electrode, and the reference electrode are all configured to be in electronic communication when the contact lens is worn on the user's eye; and (d) a communications module configured to:
    (i) process the power signal from the antenna to provide operational power to the biosensor module; and
    (ii) process the biosensor signal to provide the data signal to the LED.

In another aspect, a powered contact lens is provided. In one embodiment, the powered contact lens is formed from a transparent substrate shaped to be worn directly over a user's eye, the contact lens comprising:

(a) a photovoltaic device disposed at a margin of the contact lens, wherein the photovoltaic device is configured to provide a power signal to the contact lens when exposed to electromagnetic radiation;

(b) a light-emitting diode (LED) configured to transmit a data signal;

(c) a biosensor module configured to measure a characteristic of the user's eye, the biosensor module comprising and electrochemical sensor comprising:
  (i) a working electrode;
  (ii) a counter electrode;
  (iii) a reference electrode; and
  (iv) a biosensor circuit configured to measure the voltage of the working electrode, the counter electrode, and the reference electrode, and to transmit a biosensor signal;
  wherein the working electrode, the counter electrode, and the reference electrode are all configured to be in electronic communication when the contact lens is worn on the user's eye; and
(d) a communications module configured to:
  (i) process the power signal from the photovoltaic device to provide operational power to the biosensor module; and
  (ii) process the biosensor signal to provide the data signal to the LED.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 8A-8D: Solar cell fabrication and assembly results. FIG. 8A: Microscope image of micro solar cells on the carrier wafer after metallization and isolation and prior to their release. On each cell, a central p\contact is surrounded by four n contacts so that cells operate in any orientation after assembly on the contact lens. FIG. 8B: Released solar cells stored in deionized water. FIG. 8C: Microscope image of four cells assembled in parallel. FIG. 8D: Microscope image of four cells assembled in series.

FIG. 26: Pulse generator for a backscatter modulator (26A) and a LED driver (26B).

DETAILED DESCRIPTION

The present invention provides devices having features deposited on two sides of a device substrate, and methods for making the same. The devices are useful, for example, as the components in a macroelectronic system. The devices are also useful in microelectronic systems. In a preferred embodiment, the devices are photosensors having a plurality of electrodes patterned on a first side of the device and an electromagnetic interference filter patterned on a second side of the device. The method facilitates the fabrication of two-sided micro components through the use of an immobilizing layer deposited on top of devices patterned on a first side of a device substrate; flipping the device substrate; processing the second side of the device substrate to produce patterned features on the second side of the device substrate; and releasing the devices having patterned elements on two sides of each device.

In one aspect, a fabrication method is provided for processing features on two sides of a device substrate. In one embodiment, the method includes the steps of processing a first side of a device substrate such that at least one device area is formed; coating the first side of the device substrate with an immobilizing material to provide an immobilizing layer; inverting the device substrate to provide processing access to a second side of the device substrate; removing material from the second side of the device substrate until the device substrate supporting the at least one device area is a desired thickness, wherein the second side of the device substrate is opposite the first side of the device substrate; processing the second side of the device substrate, including the at least one device area; and removing the immobilizing layer to provide at least one device having processed features on both a first side of the device and a second side of the device, wherein the first side of the device is opposite the second side of the device.

Figure 1:
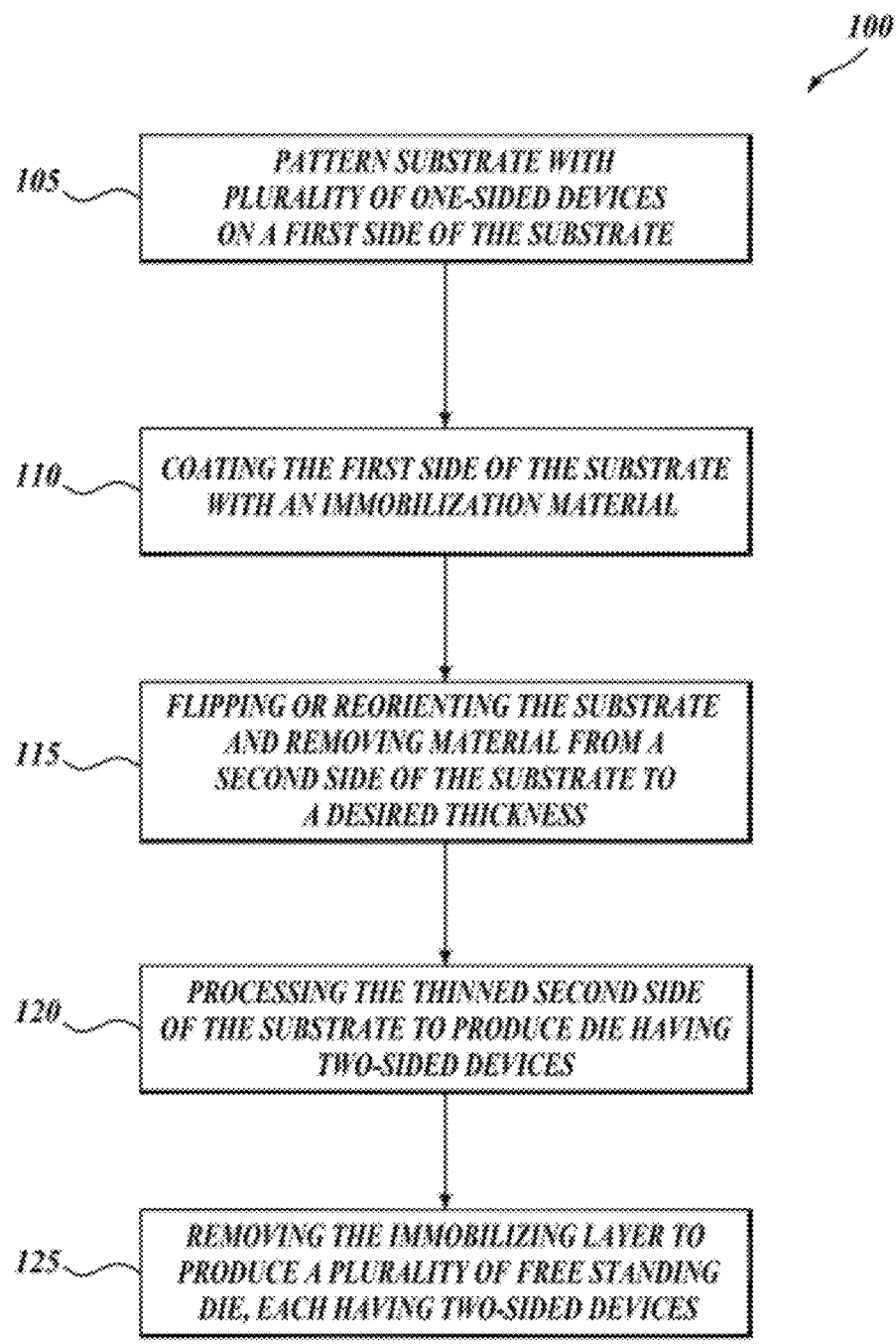
FIG. 1 is a flow chart of a representative method for fabricating a device having processed features on two sides of the device, in accordance with the present invention.

The method will be better understood with reference to FIG. 1, a flow chart describing the steps of the method 100. The method 100 begins with patterning a plurality of one-sided devices on a first side of a substrate 105. The substrate can be any material known to those of skill in the art as being processable by semiconductor processing techniques, including but not limited to crystalline and polycrystalline semiconductors, glass, polymer, and ceramics. Representative semiconductor processing techniques include lithography (e.g., photolithography and soft lithography), thin film deposition techniques (e.g., spin coating, vapor deposition, sputtering, and electron beam deposition), and etching (e.g., reactive ion etching and solvent etching). Typical substrates include semiconductor substrates, such as silicon, doped silicon, silicon-on-insulator (SOI), III-V semiconductors (e.g., gallium arsenide); polymer substrates; glasses and other inorganic substrates; and composite substrates that include two or more materials. Substrates having buried layers (e.g., the oxide layer of an SOI wafer) comprised of a different material than the bulk of the substrate are useful because the buried layer can act as an etch stop during processing, as described in more detail below.

A plurality of one-sided devices are typically patterned on the substrate, each device being the same or one of a plurality of different devices. Devices can be any electronic, optical, optoelectronic, or any other device known to those of skill in the art. Because the final product of the method 100 is a two-sided device, typical devices include those devices that require, or are enhanced by having, features patterned on a second side of the device (other than that exposed and patterned at the beginning of the method 100). A representative example of a two-sided device is a photosensor having electrodes patterned on a first side and an electromagnetic filter patterned on the second side, as will be described in more detail below.

The first side of the substrate is then coated with an immobilizing material 110 that is typically also a planarizing material. The material is typically deposited in a liquid or vapor form. Any immobilizing material can be used as long as it suitably immobilizes the patterned devices and allows the substrate to be processed as further described in the method 100. Typical immobilizing materials include polymethylmethacrylate (PMMA) and polydimethyl siloxane (PDMS).

Because further steps of the method (115, 120, and 125) require the substrate to be "flipped" or otherwise reoriented for processing on a second side, the immobilizing layer is typically augmented by attaching an immobilizing substrate, or "handle" wafer to the immobilizing layer. The immobilizing substrate tightly binds to the immobilizing layer, thus allowing the device substrate and immobilizing layer to be reoriented, e.g., flipped such that a second side of the device substrate is accessible for processing.

The method 100 continues in block 115, where the flipping of the substrate and subsequent processing proceeds. Using similar semiconductor processing techniques as those described above, the substrate is processed such that material is removed from the device substrate in those areas desired by the user (typically through the use of lithographic patterning and etching techniques) until the device substrate has a desired thickness.

In a current embodiment, the desired thickness of the device substrate is on the order of nanometers or micrometers. In a representative embodiment, the desired thickness of the device substrate is less than 50 microns. In a representative embodiment, the substrate is an SOI wafer having a top device layer of silicon, a middle layer of silicon dioxide, and a bottom carrier layer of silicon. The substrate is flipped such that the bottom carrier layer is accessible, e.g., oriented as the top surface and the carrier silicon is patterned using photolithography and etched using reactive ion etching. Because silicon and silicon dioxide are etched at different rates by typical reactive ion etching processes, the etching process essentially ceases when the carrier silicon is completely etched and the middle silicon dioxide layer is exposed. The silicon dioxide layer is then solvent etched (for example, with hydrofluoric acid), finally revealing the underside of the device layer of the SOI substrate. Thus, in this representative example, the depth to which the device substrate is thinned in the step of block 115 directly correlates to the thickness of the device layer of the SOI wafer.

The second side of the thinned device substrate is then processed 120. Further processing of the exposed second side of the device proceeds using processing techniques known to those of skill in the art as described above. The product of the processing in block 120 is a plurality of die, each having at least one device having features patterned on both a top side and bottom side of the device substrate. In representative examples discussed herein, such as photosensors, the device features on both sides combine to enhance or enable the device properties. For the exemplary photosensors, the electrodes patterned on the first side of the photosensor help to attach the photosensor to a substrate for macroelectronic devices (e.g., through self-assembly) and also to drive the photosensing function of the device. In this representative example, a filter is patterned on the second side of the photosensor, which enables the selection of the wavelength of electromagnetic radiation that impinges on the photosensor, thus acting as a wavelength filter for the device.

In other exemplary embodiments of two-sided devices, the devices can be in communication (e.g., electronic or optical) between the first side and the second side of the device. Or, the sides can be separate, with each side having a function independent of the other. Vias can be passed through the substrate of the device, electrically connecting the first side and the second side of the device, or semiconducting and/or insulating regions can be created in the device substrate.

In the final step of the method 100 at block 125, the immobilizing layer is removed to produce free-standing die. By removing the immobilizing layer, the individual die having two-sided devices are released from their processing carriers (i.e., the immobilizing layer and any attached substrate) such that the individual devices are no longer physically attached to other devices. Removing the immobilizing layer typically includes a solvent bath that dissolves the immobilizing layer. In a representative example, when the immobilizing layer is PMMA, an organic solvent (such as acetone) can be used to dissolve the immobilizing layer and release the die.

After the two-sided devices have been fabricated using the method 100, such devices may be useful, for example, in fluidic self-assembly systems, such as those described above with regards to International Patent Application Nos. PCT/US2007/072038 and PCT/US2008/050104.

Figure 2A:
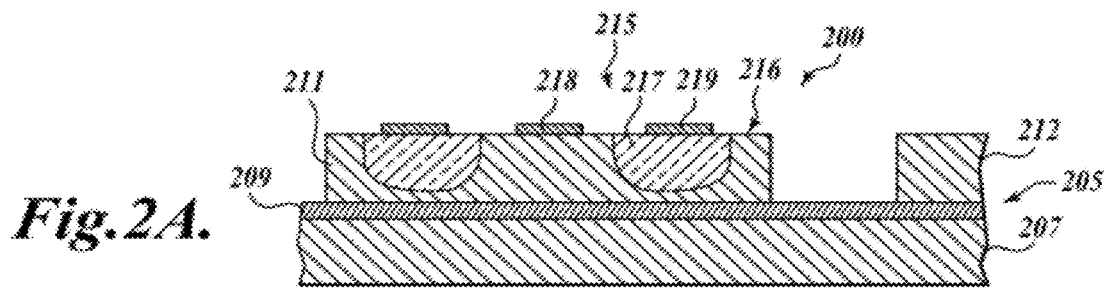
FIGS. 2A-2H illustrate the fabrication of a representative two-sided device in accordance with the method illustrated in FIG. 1.

The method described with regard to FIG. 1 will now be more specifically applied to a representative device fabrication of a photosensor having electrodes disposed on one side of the device and an electromagnetic filter disposed on the second side of the device. Referring now to FIG. 2A, a device substrate 200 includes an SOI wafer 205 from which a representative one-sided device 215 is fabricated, the one-sided device 215 having a first side 216 facing upwards. The SOI wafer 205 has a carrier layer 207, a buried oxide layer 209, and a device layer 211 in which the one-sided device 215 is formed. The one-sided device 215, in this exemplary embodiment, is a photosensor having a doped annular silicon region 217, an annular electrode 219, and a center electrode 218. In this representative example, the device layer 211 of the SOI wafer 205 is a p-type semiconductor substrate (such as boron-doped silicon), and the doped regions 217 include an n-type dopant (such as phosphorus). An edge portion of a neighboring device 212 is also shown.

As illustrated in FIG. 2A, the patterned device substrate 200 includes one one-sided photosensor device 215, which remains attached to the SOI substrate 205 at the oxide layer 209.

Figure 2B:
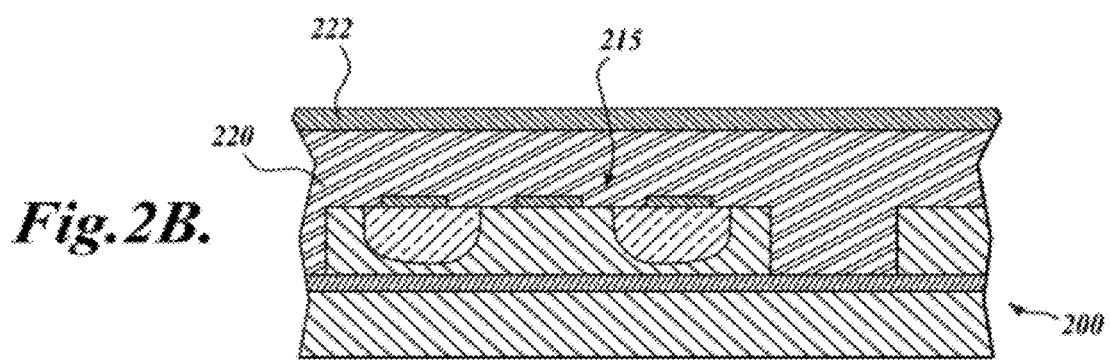

Referring now to FIG. 2B, an immobilizing layer 220 is deposited on top of the device substrate 200, including the attached one-sided photosensor device 215. As shown in FIG. 2B, an optional handle wafer 222 is attached to the immobilization layer 220 to aid in further processing steps. While only one photosensor device 215 is illustrated, it will be appreciated that the FIGS. 2A-2H show only a portion of the device substrate 205, which typically contains multiple devices (e.g., neighboring device 212), and can include multiple types of multiple devices. Although a single complete device is shown in FIGS. 2A-2H, the method is not limited to such.

Figure 2C:
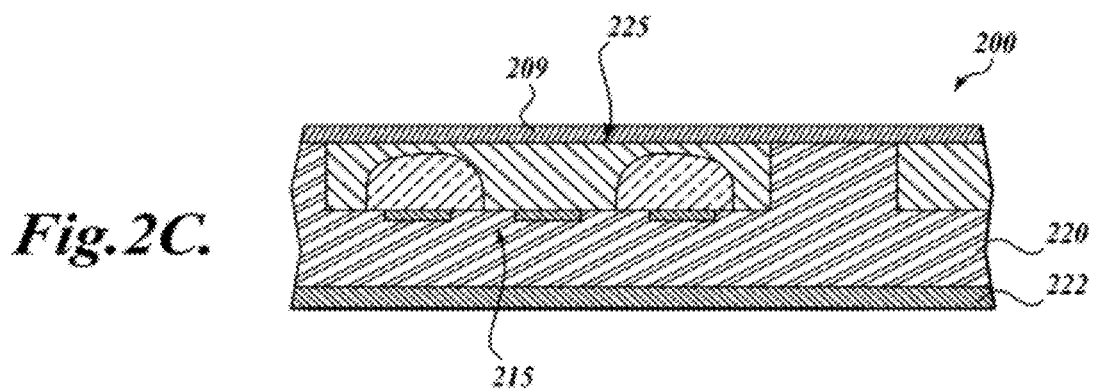

Referring now to FIG. 2C, the entire device substrate 200, immobilization layer 220, and handle 222 have been flipped or otherwise reoriented such that the handle 222 is the "bottom" layer of the device substrate 200. In FIG. 2C, the carrier layer 207 has been patterned (for example, by photolithography) and etched (for example, by reactive ion etching) such that a second side 225 of the photosensor device 215 has had the carrier layer 207 above it etched until only the oxide layer 209 remains above the device 215. Portions of the carrier layer 207 may remain on the oxide layer 209, although the no carrier layer 207 remains in the embodiment illustrated in FIG. 2C.

Figure 2D:
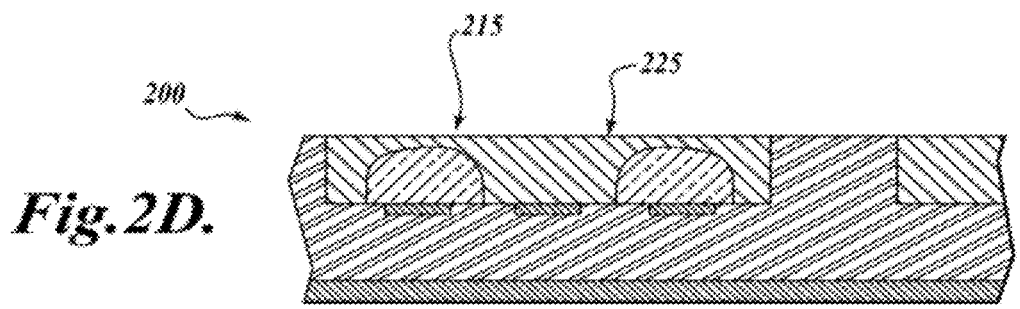

Referring now to FIG. 2D, the oxide layer 209 is etched, typically by a solvent-based process, such as hydrofluoric-acid etching. With the removal of the oxide layer 209, any the remaining portions of the carrier layer 207 (not illustrated) on the device substrate 200 are removed and the second side 225 of the photosensor device 215 is exposed for further processing.

Figure 2E:
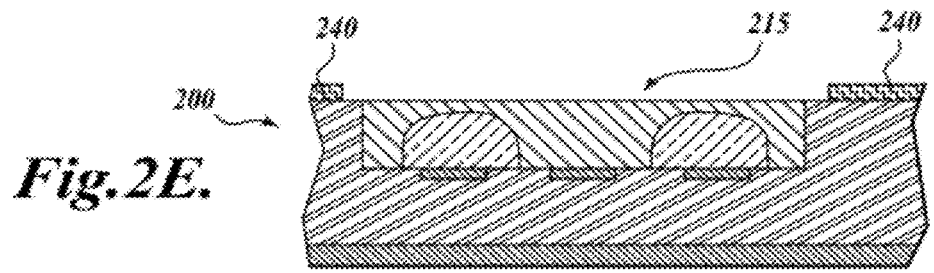

Referring now to FIG. 2E, a lithographic mask 240 is shown having patterned areas covering portions of the device substrate 200 but leaving the area above the photosensor device 215 exposed for further processing.

Figure 2F:
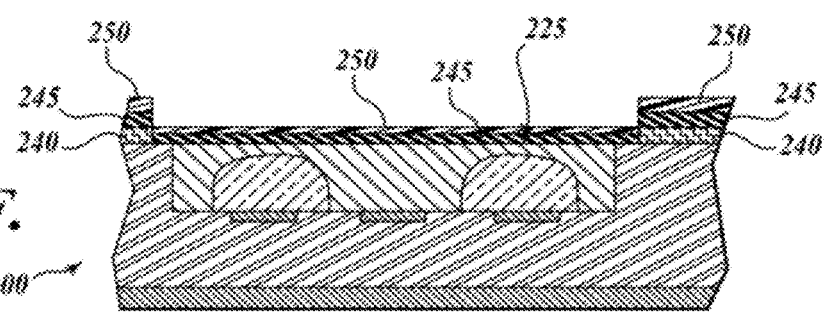
Figure 2G:
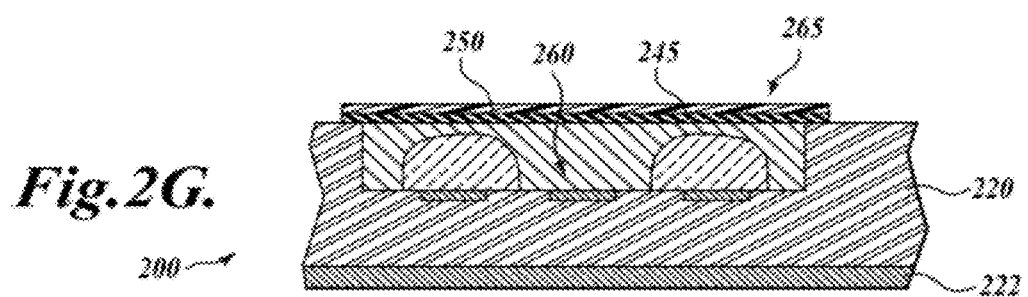
Figure 2H:
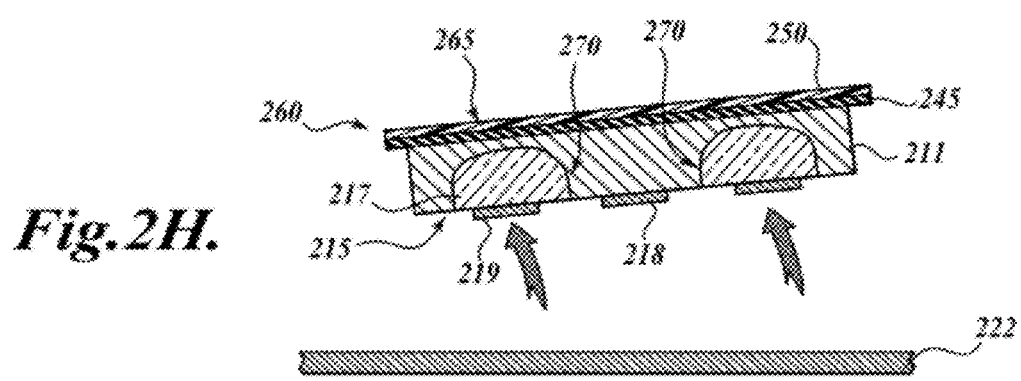

Referring now to FIG. 2F, thin film deposition is used to deposit multiple layers of materials 245 and 250 having different dielectric constants. The thin film layers 245 and 250 are useful as an electromagnetic filter (such as an interference filter), and typically such a filter requires a plurality of alternating thin film layers of materials having distinct dielectric constants. While only one bilayer (245 and 250) is illustrated in FIGS. 2F-2H, for simplicity, a typical interference filter would have several more alternating layers of layer 245 and layer 250. The layers 245 and 250 are deposited on the second side 225 of the device 215 and also on top of the patterned photomask 240.

Referring now to FIG. 2G, the photomask 240 illustrated in FIG. 2F has been used as a lift off mask, and the bilayer 245 and 250 covering the photomask 240 is removed from the device substrate 200 when the photomask is exposed to an appropriate solvent to dissolve the photomask material. The remaining structure, illustrated in FIG. 2G, is a filtered photosensor device 260 having an articulated bilayer 245 and 250 covering the second side 225 of the filtered photosensor device 260.

Finally, as illustrated in FIG. 2H, the completed device 260 is released by etching (or dissolving) the immobilization layer 220 to an extent that allows for the release of the immobilized devices 260 as individual die.

The released photosensor devices 260 are fully functioning photosensor devices having features patterned on two sides (215 and 225) of the device, wherein the two sides are opposite of each other. On the first side 215 of the device, electrodes 218, 219 are patterned, and on the second side 225 of the device, an electromagnetic filter 265 is comprised of a bilayer of two thin films 245 and 250 having distinct dielectric constants. A p-n junction 270 is created in the device 260 through the use of a p-doped substrate 211 and n-doped regions 217. Light impinging on the device from the side of the filter 265 will be selectively filtered, based on wavelength, in a manner known to those of skill in the art. The thicknesses and compositions of the layers 245 and 250 of the filter 265 determine the filter 265 properties. A plurality of free-standing photosensor devices 260 can further be self-assembled onto a macroelectronic substrate to form a portion of a macroelectronic device.

Figure 3:
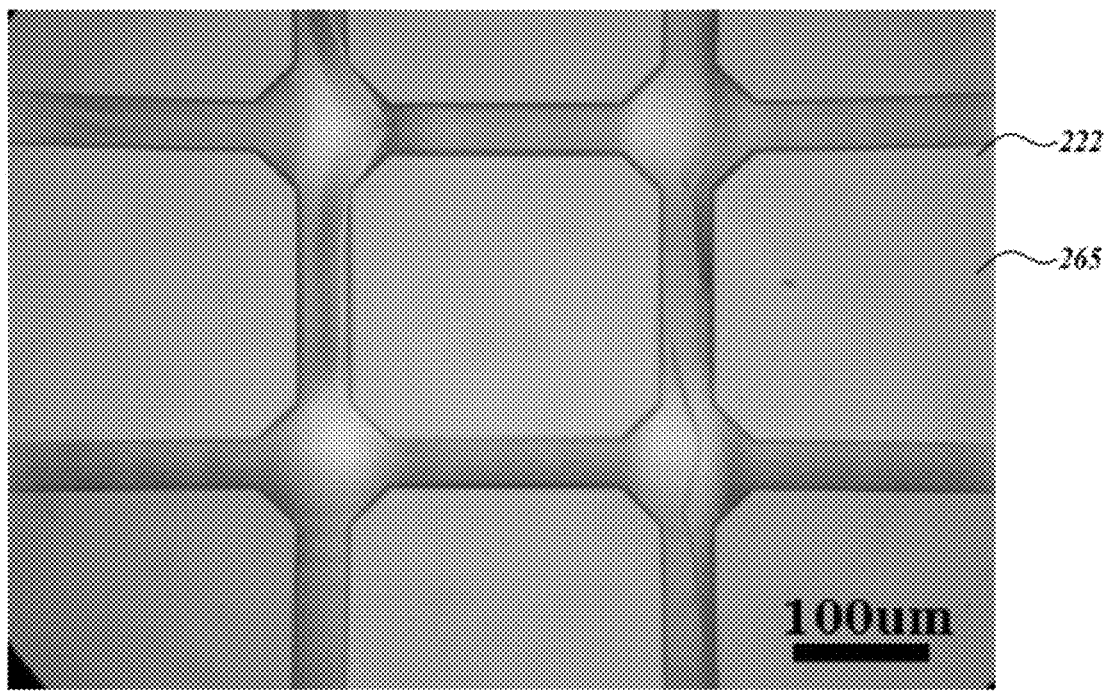
FIG. 3 is a micrograph of representative photosensor devices prior to release from a substrate after partial fabrication in accordance with the method of the invention.

Referring now to FIG. 3, a micrograph is shown of a representative substrate fabricated by a partial method as described herein. In the micrograph, the electromagnetic filters 265 as described with regard to FIGS. 2G and 2H can be seen. Because this micrograph is an image captured during a portion of fabrication of photosensor devices, as described in conjunction with FIGS. 2A-2H, it will be appreciated that FIG. 3 is an image corresponding substantially to the diagrammatic depiction of FIG. 2G. Looking at the device substrate 200 in plan view, the micrograph in FIG. 3 shows the electromagnetic filter 265 and the immobilization layer 222 in between the articulated devices.

Figure 4:
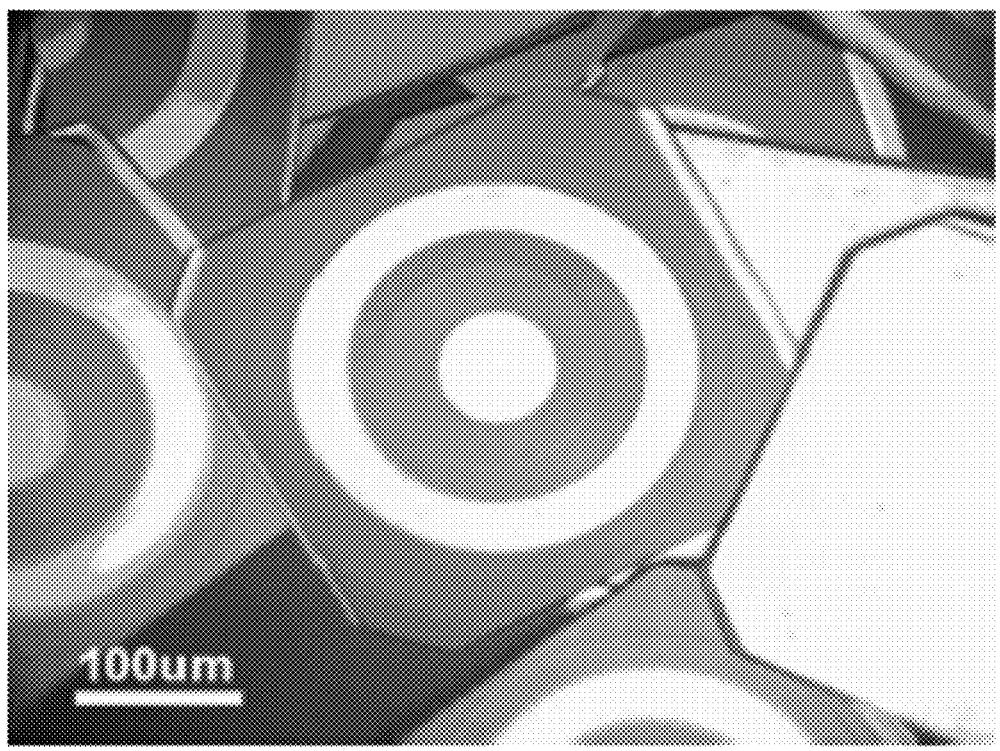
FIG. 4 is a micrograph of multiple free-standing photosensor elements in accordance with the present invention having integrated filter elements, wherein the electrodes form a target pattern on a first side of the device and the photosensor filter is formed on the second side of the device.

Referring now to FIG. 4, released two-sided photosensor component die (e.g., devices 260 as illustrated in FIG. 2H) are shown in the micrograph. The target-like structure corresponds to electrodes on the photosensor (e.g., 219), and the homogenous colored sides of the devices are electromagnetic filter elements (e.g., 265).

Figure 5:
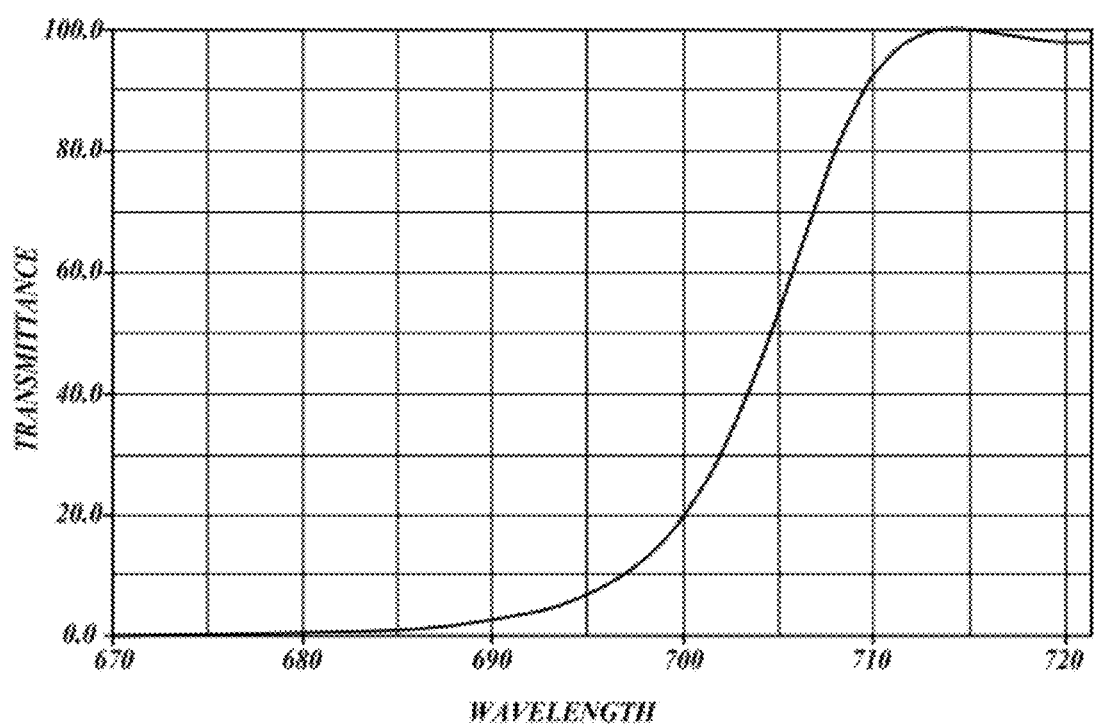
FIG. 5 is a chart plotting the transmittance characteristics of a representative electromagnetic filter formed on one side of a two-sided device in accordance with the present invention.

Referring now to FIG. 5, a transmittance versus wavelength chart for a representative photosensor is illustrated. The filter allows only wavelengths greater than about 700 nanometers to pass through the filter. The filter analyzed in FIG. 5 was fabricated using the method described herein with regard to FIG. 1 and FIGS. 2A-H. The filter was fabricated by depositing about twelve bilayers comprising alternating layers of silicon dioxide and tantalum pentoxide, wherein each bilayer includes about 80 nanometers of tantalum pentoxide and about 108 nanometers of silicon dioxide. In this representative example, both oxide layers were fabricated using a low-temperature deposition process where the temperature did not exceed 100 degrees Celsius, so as to not damage the immobilization layer (e.g., PDMS).

The immobilization layer has been previously described and can include polymers such as PMMA and PDMS. It will be appreciated that PDMS is a preferred immobilization layer for many applications because of its resistance to many of the chemicals used in semiconductor manufacturing processes. For example, acetone is an organic solvent commonly used to remove photoresist, and if PMMA is used in the method as an immobilization layer, then removal of the photoresist (with acetone or a similar solvent) will also remove the immobilization layer. For some fabrication processes, such a simultaneous dual removal (of photoresist and the immobilization layer) may be acceptable, or even desirable in terms of both time and material efficiency. However, if the photoresist and immobilization layer would preferably be removed separately, an immobilization layer such as PDMS may be preferable. PDMS is typically removed using the solvent tetra-n-butylammonium fluoride (TBAF).

The solvent used to dissolve the immobilizing layer is typically also used to store the released free-standing two-sided devices. In the exemplary system described above where PDMS is the immobilizing layer, TBAF is used to dissolve the PDMS layer and release the components. The components are then captured (for example, by filtration) and then stored (for example, in a vial) in water. As described above, the free-standing devices can then be used in an assembly method, such as fluidic self-assembly, for assembling more complex structures, including macroelectronic devices.

In one embodiment, a device fabricated by the method of invention is provided. The device is fabricated on a substrate having a first device side and a second device side, wherein the first device side is opposite the second device side, and wherein the device has features disposed on both the first device side and the second device side. In a further embodiment, the device is a photosensor having a plurality of electrodes patterned on the first device side and an interference filter deposited on the second side of the device.

In another aspect, a semiconductor device is provided that is fabricated from a silicon-on-insulator substrate including a device layer, a buried oxide layer, and a carrier layer, wherein the device is fabricated in the device layer, the device having device features disposed on both a top side of the device and a bottom side of the device, and wherein the features on the bottom side of the device are formed after removal of the buried oxide layer and the carrier layer.

In another aspect, a device is provided that is fabricated on a substrate having a first device side and a second device side, wherein the first device side is opposite the second device side, wherein the device has features disposed on both the first device side and the second device side, wherein the substrate has a thickness dimension of less than about 50 microns.

Devices have features patterned on two opposite sides of a device substrate. The method described above enables the patterning of features on a first and second side of the device substrate. Traditional semiconductor processing techniques cannot produce devices such as those described herein. By "flipping" the substrate, as aided by the immobilization layer technique described above, two sides of a device substrate can be processed by microfabrication techniques. The materials used to form the substrate of the device are not typically important and include semiconductors, insulators, conductors, and compounds of one or more of the previous material types.

A "processed feature," as used herein, refers to a feature on a surface of a substrate that has been formed using two or more microfabrication techniques. Microfabrication techniques have been described above and are known to those of skill in the art. Exemplary process features include an interference-based electromagnetic filter deposited by lift off mask photolithography and alternating thin film deposition methods. An additional exemplary process feature is an electrode structure deposited using metal deposition, photolithography, and metal etching.

Because the components are typically useful in fluidic self-assembly of macroelectronic components, the components provided herein are typically nanometers or micrometers thick, and micrometers in length and width. In one embodiment, the components are less than 500 microns thick. In a preferred embodiment, the components are less than 50 microns thick. In a further preferred embodiment, the components are less than 10 microns thick. Such thin substrates result in unusually small free-standing components and consume an economic amount of substrate in production when compared to traditional components of the same type.

The types of devices that can be fabricated on each of the two sides of the components include such electrical, optical, and electro-optical devices as transistors, diodes, resistors, light emitting diodes (LEDs), and photosensors. Some device structures, such as those illustrated as the free-standing component 260 illustrated in FIG. 2H, can be useful as multiple types of components. The component in FIG. 2H, 260, includes processed features on both a first side and second side, including an interference filter 265 and electrodes 219. The p-n junction 270 created by the different doping types of the substrate 211 and doped regions 217 results in a component that can be used as both a photosensor and a light emitting diode, depending on the biasing of the electrodes 219. If the component 260 is used as a photosensor, the filter 265 will limit the light impinging on the photosensor to a particular spectrum, whereas if the component 260 is used as a light emitting diode, the filter 265 will act to filter out a portion of the spectrum emitted by the device 260.

A free-standing die can include one or more devices. A single device structure 260 on a die is illustrated in FIG. 2H. The single device structure 260 includes features patterned on both sides of the device which operate in tandem to produce a single effect (e.g., photosensing). It will be appreciated that each side may have its own independently functioning component or device, and each side may have multiple features patterned on a side that form one or more devices, some of which may act in conjunction with features formed on the opposite side of the device.

In another aspect, a free-standing photosensor is provided, comprising a first side having an outer electrode surrounding an inner electrode and a second side having an electromagnetic filter, wherein the photosensor is adapted for self-assembly onto a substrate through a self-assembly means.

Photosensor devices are provided having features patterned on both sides of a device substrate. As described in the method above, electrodes are patterned on a first side of a device substrate, and an electromagnetic filter is patterned on the second side of the device substrate. The device substrate itself is a semiconductor material having either n- or p-doping, and at least one region beneath an electrode in the substrate has the opposite doping as that of a substrate. The resulting junction between p- and n-type semiconductors yields a photosensor device structure. The photosensor is driven by the electrodes, which are interfaced with the proper equipment for detecting a photosignal (e.g., a multimeter). The filter can be customized to select the spectrum of light allowed to pass through the filter and impinge on the device sensing structure. A typical photosensor is illustrated in FIG. 2H, with the photosensor 260 having electrodes 219, a filter 265, a substrate 211, and doped regions 217.

The photosensor can be fabricated from any material that can produce a photo current. Typically, crystalline, semicrystalline, or long crystalline semiconducting materials are used to fabricate photosensors. Typical photosensing materials include silicon, gallium arsenide (GaAs), aluminum gallium arsenide (AlGaAs), indium phosphide (InP), and silicon germanium (SiGe). The type of material, as well as type of filter used for a photosensor, are known to those of skill in the art. For example, different materials, as described above, have greater or lesser sensitivities in spectral regions such as visible, infrared, and ultraviolet. Additionally, materials may be selected for the speed at which they react to impinging light.

In another aspect, solar cells attached to a contact lens are provided. In one embodiment, the solar cells are made using a "two sided" process as disclosed above (e.g., in FIGS. 1-2H). By using the two-sided process, solar cells of only a few microns in thickness can be fabricated. Such relatively thin solar cells can be incorporated into a contact lens without discomfort to the wearer. Particularly, the thin solar cells are thinner than the thickness of the contact lens and so can be embedded or otherwise attached to the contact lens such that the solar cell does not alter the thickness profile of the contact lens in such a way that the wearer of the contact lens is affected.

In one embodiment, a powered contact lens is provided that includes a transparent substrate having a plurality of recesses shaped to be worn directly over a user's eye, a photovoltaic component disposed in one of the plurality of recesses, and an electronic component disposed in another of the plurality of recesses, wherein the photovoltaic component is in electronic communication with the electronic component, and wherein the photovoltaic component has a p contact and an n contact on only a first side of the photovoltaic component.

The contact lens is shaped to be worn by a user, and, therefore, the transparent substrate, which defines the shape of the contact lens, is shaped to be worn directly over a user's eye. As such, the transparent substrate has an inner surface, shaped to abut a user's eye, and an outer surface, shaped to generally mimic the curvature of the user's eye, so as to not irritate the user's eyelid when it closes. Because both the eye and the eyelid must be affected as little as possible by the contact lens, the recesses in the contact lens allow the photovoltaic component and the electronic component to be embedded in the transparent substrate such that all parts of the components are contained below the surface (both inner and outer). That is, no parts of the components project beyond the surfaces of the contact lens, which reduces irritation of the eye and eyelid.

The electronic component can be any electronic device known to those of skill in the art that requires power that can be supplied, at least partially, by the photovoltaic component. The contact lens is a "powered" contact lens because it contains photovoltaic components to supply power. The supplied power is used for one or more electronic components. Exemplary electronic components include radio-frequency communication devices, processors, memory for storing data, and analytical devices for testing the composition of substances (e.g., tears) which come into contact with the contact lens.

The photovoltaic component need not provide all of the power to the electronic component(s), as batteries, RF receivers, or other supplemental power sources can be used. However, in one embodiment, one or more photovoltaic components provide all of the power used by the electronic component(s) on the contact lens.

The photovoltaic component can be any photovoltaic component having a p/n junction, known to those of skill in the art. It will be appreciated that while the described embodiments generally relate to traditional, inorganic photovoltaic materials (e.g., silicon p/n junction photovoltaics), any component capable of generating electricity through conversion of electromagnetic radiation is contemplated. Particularly, organic photovoltaic materials may not have a p/n junction, but such materials can be incorporated into the devices described herein.

The p contact and n contact of the photovoltaic component can be the p-type and n-type materials themselves (e.g., p- and n-doped silicon), or the contacts can be conductors deposited in electrical contact with the p-type and n-type materials on the device. For example, in Example 1, the p/n junction of the photovoltaic device is created by using a p-type silicon wafer and creating n-type regions through targeted diffusion into areas of the silicon wafer. Metal contacts (either the same metal for each type of contact, or different), are then used to facilitate ohmic contact to the silicon, as well as bonding to the transparent substrate of the contact lens.

The p and n contacts are disposed on the same side of the photovoltaic component, so as to provide a "one-sided" device. The contacts are on one side of the device to facilitate attachment of the photovoltaic device to the transparent substrate (e.g., using the method described below. In certain embodiments, the transparent substrate comprises an interconnect network that electronically links at least one photovoltaic component to at least one electronic component. The interconnect network can be embedded within the transparent substrate, such that it is shielded from the environment outside of the contact lens. The one-sided electrodes of the photovoltaic component interface with the interconnect network in a "flip-chip" manner, but attaching both the p and n contacts on the same surface of the photovoltaic component, instead of having one contact on one surface of the device and the other contact on the other surface, which greatly would complicate attachment of such a small component into the transparent substrate.

In one embodiment, the p contact and the n contact are coplanar. As used herein, the term "coplanar" means that the contacts are in the same plane. That is, the same lateral height off of a common surface of the component.

In one embodiment, the photovoltaic component has a thickness of 50 microns or less. In another embodiment, the photovoltaic component has a thickness of 10 microns or less. The photovoltaic components are relatively small, so as to fit one or more into a contact lens, which is a section of a sphere having a radius of about 1-2 cm. The components are typically less than 1 mm at the largest dimension, and are preferably less than 0.5 mm at the largest dimension.

In one embodiment, the contact lens includes a plurality of photovoltaic components, wherein each of the plurality of photovoltaic components are disposed in a corresponding one of the plurality of recesses. An interconnect network can also be disposed on the transparent substrate that electronically connects the plurality of photovoltaic components and the electronic component. In one embodiment, at least two of the plurality of photovoltaic components are electronically connected in series. In another embodiment, at least two of the plurality of photovoltaic components are electronically connected in parallel.

In one embodiment, the transparent substrate is a polymer substrate. The transparent substrate is a material that is compatible with making a contact lens, in shape, transparency, durability, and biocompatibility. If the transparent substrate does not satisfy one or more of the requirements for a contact lens (e.g., biocompatibility), then a coating ("encapsulation") can be used to coat the entire transparent substrate, wherein the coating remedies the deficiencies of the transparent substrate (e.g., the coating is biocompatible).

The photovoltaic component is embedded in the transparent substrate and may also be enclosed within the substrate. In certain embodiments, an encapsulation layer overlying the substrate and abutting a second side of the photovoltaic component is provided. The encapsulation layer can be a conformal layer that covers the entire contact lens, or can be formed so as to only encapsulate the photovoltaic components in the recesses. Encapsulation materials are compatible with the various fluids produced and encountered by the human eye (e.g., tears, water, blood). Representative encapsulation materials include polymers such as parylene.

In another aspect, a method for fabricating a thin solar cell device having a p contact and an n contact on only one surface of a device substrate is provided. In one embodiment, the method includes the steps of:

processing a first side of the device substrate such that at least one photovoltaic component is formed, the photovoltaic component comprising a p contact adjacent a p-type semiconductor region of the device substrate and an n contact adjacent an n-type semiconductor region of the device substrate, wherein the p contact and the n contact are both on the first side of the device substrate;

coating the first side of the device substrate with an immobilizing material to provide an immobilizing layer;

inverting the device substrate to provide processing access to a second side of the device substrate;

removing material from the second side of the device substrate until the device substrate supporting the at least one photovoltaic device is a desired thickness, wherein the second side of the device substrate is opposite the first side of the device substrate; and removing the immobilizing layer to provide at least one released photovoltaic component having the p contact and the n contact on only the first side of the device substrate.

The method can be used to fabricate a photovoltaic component that is sized (microns thick) and configured (n and p contacts on one side of the component) to be integrated into a contact lens to provide on-lens power.

In one embodiment, the method further includes a step of processing the second side of the device substrate, as described above in previous aspects.

In one embodiment, the device substrate is an SOI wafer having a carrier layer of silicon, a buried sacrificial layer comprised of a silicon oxide, and a device layer of silicon, wherein the first side of the device substrate is the device layer of silicon and the second side of the device substrate is the carrier layer of silicon, and wherein removing material from the second side includes etching the carrier layer of silicon until at least a portion of the sacrificial layer is exposed and then etching the sacrificial layer until it is substantially removed.

The thickness of the released photovoltaic component is less than about 50 microns, and, preferably, less than 10 microns.

In one embodiment, the method further comprises forming a powered contact lens by attaching the photovoltaic component to a transparent substrate shaped to be worn directly over a user's eye, wherein the p contact and the n contact of the photovoltaic component are in electrical communication with an interconnect network on the transparent substrate.

The photovoltaic devices, powered contact lenses, and the methods for making both will now be discussed in detail with reference to FIGS. 6-13.

Figure 6:
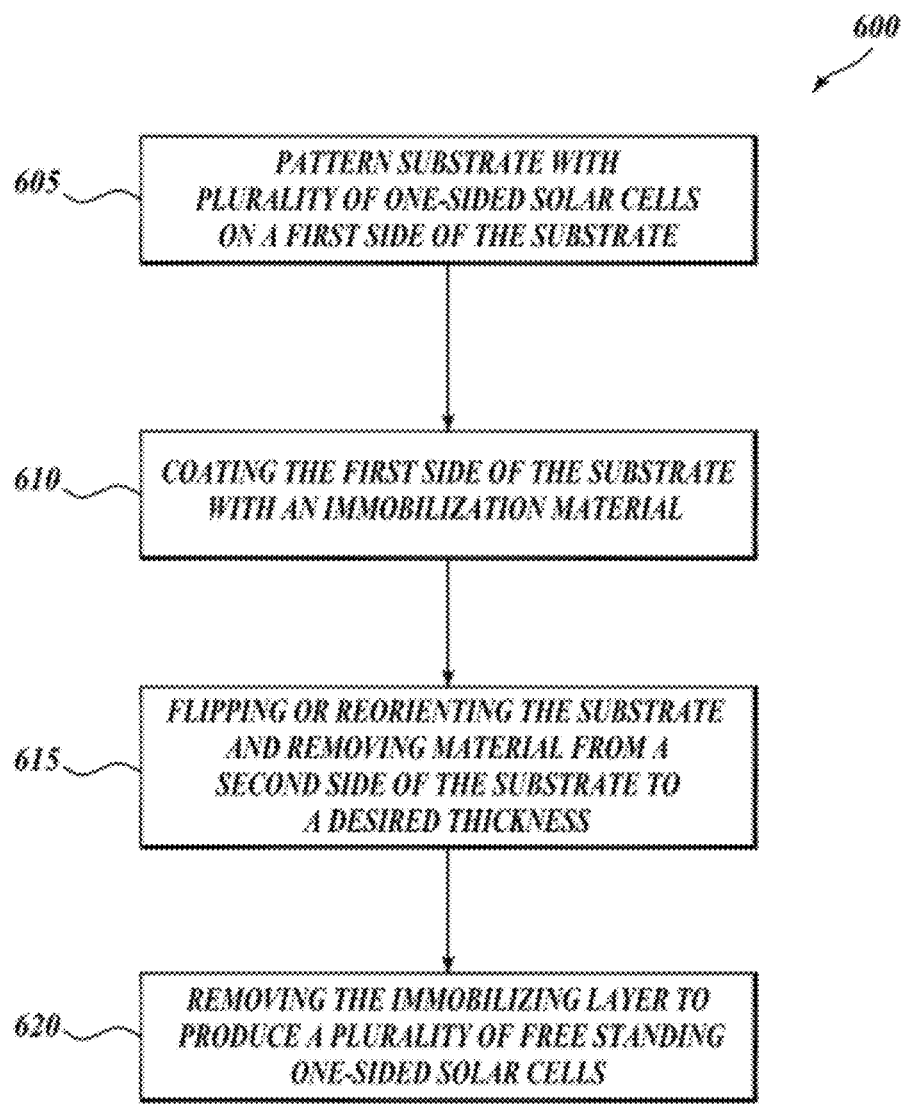
FIG. 6 is a flow chart of a representative method for fabricating a solar cell having coplanar electrodes on only one side of the device substrate in accordance with the present invention.

The method will be better understood with reference to FIG. 6, a flow chart describing the steps of the method 600. The method 600 begins with a step of patterning a plurality of one-sided solar cells on a first side of a substrate 605. The substrate can be any material known to those of skill in the art as being processable by semiconductor processing techniques, including but not limited to crystalline and polycrystalline semiconductors, glass, polymer, and ceramics. Representative semiconductor processing techniques include lithography (e.g., photolithography and soft lithography), thin film deposition techniques (e.g., spin coating, vapor deposition, sputtering, and electron beam deposition), and etching (e.g., reactive ion etching and solvent etching). Typical substrates include semiconductor substrates, such as silicon, doped silicon, silicon-on-insulator (SOI), III-V semiconductors (e.g., gallium arsenide); polymer substrates; glasses and other inorganic substrates; and composite substrates that include two or more materials. Substrates having buried layers (e.g., the oxide layer of an SOI wafer) comprised of a different material than the bulk of the substrate are useful because the buried layer can act as an etch stop during processing, as described in more detail below.

A plurality of one-sided solar cells are patterned on the substrate, each solar cell being the same or one of a plurality of different devices. The solar cells have at least one positive contact and one negative contact, so as to extract electricity from the solar cell when illuminated with electromagnetic radiation. The contacts are coplanar (i.e., substantially in the same plane) and disposed on the same major face ("first side") of the substrate.

The first side of the substrate is then coated with an immobilizing material 610 that is typically also a planarizing material. The material is typically deposited in a liquid or vapor form. Any immobilizing material can be used as long as it suitably immobilizes the patterned devices, and allows the substrate to be processed as further described in the method 600. Typical immobilizing materials include polymethylmethacrylate (PMMA) and polydimethyl siloxane (PDMS).

Because further steps of the method (615 and 620) require the substrate to be "flipped" or otherwise reoriented for processing on a second side, the immobilizing layer is typically augmented by attaching an immobilizing substrate, or "handle" wafer to the immobilizing layer. The immobilizing substrate tightly binds to the immobilizing layer, thus allowing the device substrate and immobilizing layer to be reoriented, e.g., flipped such that a second side of the device substrate is accessible for processing.

The method 600 continues in block 615, where the flipping of the substrate and subsequent processing proceeds. Using similar semiconductor processing techniques as those described above, the substrate is processed such that material is removed from the device substrate in those areas desired by the user (typically through the use of lithographic patterning and etching techniques) until the device substrate has a desired thickness.

In a current embodiment, the desired thickness of the device substrate is on the order of nanometers or micrometers. In a representative embodiment, the desired thickness of the device substrate is less than 50 microns. In a representative embodiment, the substrate is an SOI wafer having a top device layer of silicon, a middle layer of silicon dioxide, and a bottom carrier layer of silicon. The substrate is flipped such that the bottom carrier layer is accessible, e.g., oriented as the top surface and the carrier silicon is patterned using photolithography and etched using reactive ion etching. Because silicon and silicon dioxide are etched at different rates by typical reactive ion etching processes, the etching process essentially ceases when the carrier silicon is completely etched and the middle silicon dioxide layer is exposed. The silicon dioxide layer is then solvent etched (for example, with hydrofluoric acid), finally revealing the underside of the device layer of the SOI substrate. Thus, in this representative example, the depth to which the device substrate is thinned in the step of block 615 directly correlates to the thickness of the device layer of the SOI wafer.

In the final step of the method 600 at block 620, the immobilizing layer is removed to produce free-standing solar cell die. By removing the immobilizing layer, the individual die having solar cells with coplanar electrodes are released from their processing carriers (i.e., the immobilizing layer and any attached substrate) such that the individual devices are no longer physically attached to other devices. Removing the immobilizing layer typically includes a solvent bath that dissolves the immobilizing layer. In a representative example, when the immobilizing layer is PMMA, an organic solvent (such as acetone) can be used to dissolve the immobilizing layer and release the die.

After the solar cells have been fabricated using the method 600, such devices may be useful, for example, in fluidic self-assembly systems, such as those described in International Patent Application Nos. PCT/US2007/072038 and PCT/US2008/050104, and U.S. Pat. No. 7,910,934, each of which is incorporated herein by reference in its entirety.

Figure 7A:
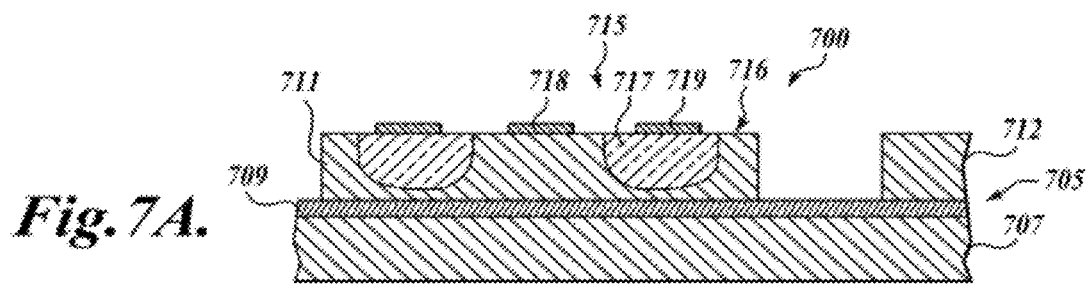
FIGS. 7A-7E illustrate the fabrication of a representative one-sided solar cell in accordance with the method illustrated in FIG. 6.

The method described with regard to FIG. 6 will now be more specifically applied to a representative device fabrication of a one-sided solar cell, as illustrated in FIGS. 7A-7E. Referring now to FIG. 7A, a device substrate 700 includes an SOI wafer 705 from which a representative one-sided device 715 is fabricated, the one-sided device 715 having a first side 716 facing upwards. The SOI wafer 705 has a carrier layer 707, a buried oxide layer 709, and a device layer 711, in which the one-sided device 715 is formed. The one-sided device 715, in this exemplary embodiment, is a solar cell (photovoltaic) having an n-doped silicon region 717, an n-electrode 719, and a p-electrode 718 connected to the device layer 711 of the SOI wafer 705, which is a p-type semiconductor substrate (such as boron-doped silicon). The n-doped regions 717 include an n-type dopant (such as phosphorus). An edge portion of a neighboring device 712 is also shown.

As illustrated in FIG. 7A, the patterned device substrate 700 includes one one-sided device 715, which remains attached to the SOI substrate 705 at the oxide layer 709.

Figure 7B:
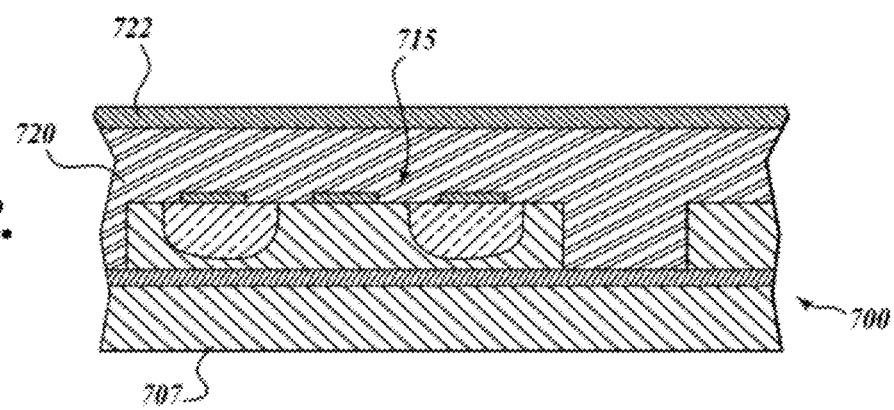

Referring now to FIG. 7B, an immobilizing layer 720 is deposited on top of the device substrate 700, including the attached one-sided device 715. As shown in FIG. 7B, an optional handle wafer 722 is attached to the immobilization layer 720 to aid in further processing steps. While only one device 715 is illustrated, it will be appreciated that the FIGS. 7A-7E show only a portion of the device substrate 705, which typically contains multiple devices (e.g., neighboring device 712), and can include multiple types of multiple devices. Although a single complete device is shown in FIGS. 7A-7E, the method is not limited to such.

Figure 7C:
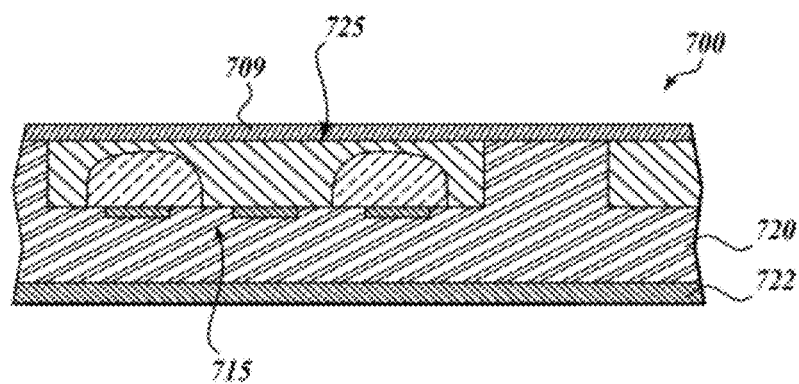

Referring now to FIG. 7C, the entire device substrate 700, immobilization layer 720, and handle 722 have been flipped or otherwise reoriented such that the handle 722 is the "bottom" layer of the device substrate 700. In FIG. 7C, the carrier layer 707 has been patterned (for example, by photolithography) and etched (for example, by reactive ion etching) such that a second side 725 of the device 715 has had the carrier layer 707 above it etched until only the oxide layer 709 remains above the device 715. Portions of the carrier layer 707 may remain on the oxide layer 709, although the no carrier layer 707 remains in the embodiment illustrated in FIG. 7C.

Figure 7D:
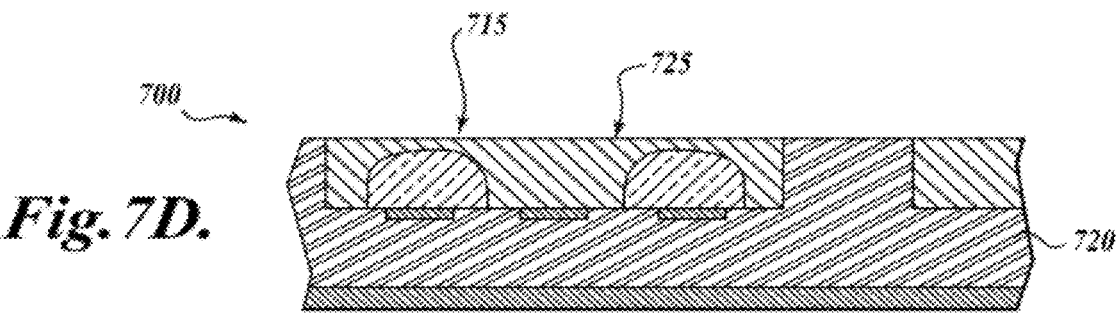

Referring now to FIG. 7D, the oxide layer 709 is etched, typically by a solvent-based process, such as hydrofluoric-acid etching. With the removal of the oxide layer 709, any the remaining portions of the carrier layer 707 (not illustrated) on the device substrate 700 are removed and the second side 725 of the device 715 is exposed.

Figure 7E:
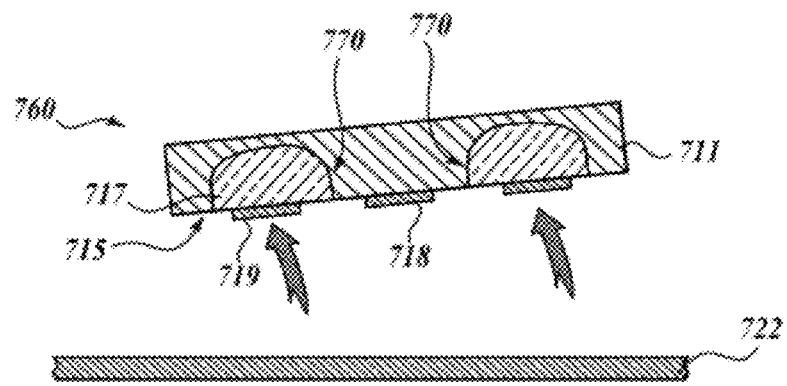

Finally, as illustrated in FIG. 7E, the completed device 760 is released by etching (or dissolving) the immobilization layer 720 to an extent that allows for the release of the immobilized devices 760 as individual die.

The released devices 760 are fully functioning solar cell devices. On the first side 715 of the device, electrodes 718, 719 are patterned to be coplanar. A p-n junction 770 is created in the device 760 through the use of a p-doped substrate 711 and n-doped regions 717. A plurality of free-standing one-sided photovoltaic devices 760 can further be assembled onto a macroelectronic substrate to form a portion of a macroelectronic device, such as a contact lens having the solar cells attached thereto.

The one-sided solar cell devices 760 can be integrated into a contact lens by any number of methods: embedding, adhesion, etc. One representative method for attaching the devices 760 to a contact lens are illustrated in FIGS. 7F and 7G, which continue the fabrication process illustrated in FIGS. 7A-7E.

Figure 7F:
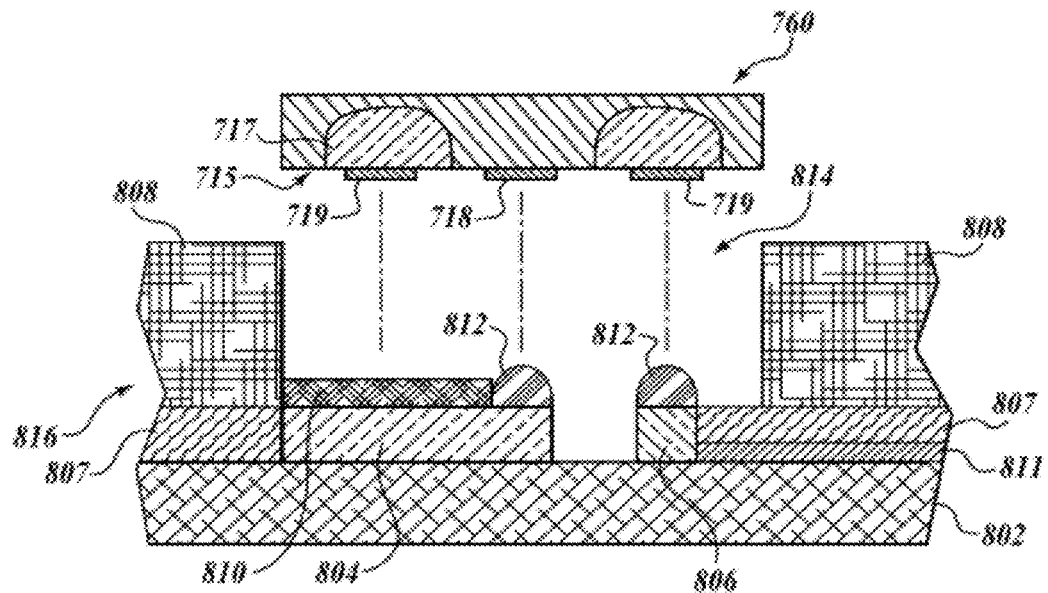
FIGS. 7F and 7G illustrate the fabrication of a representative contact lens having a one-sided solar cell (e.g., fabricated using the method of FIGS. 7A-7E) disposed thereon.
Figure 7G:
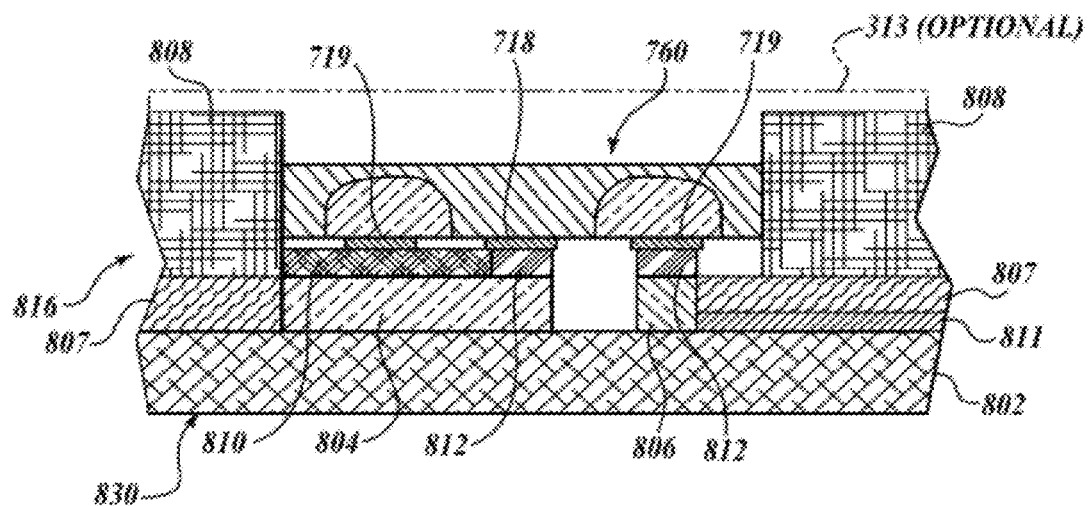
Figure 9:
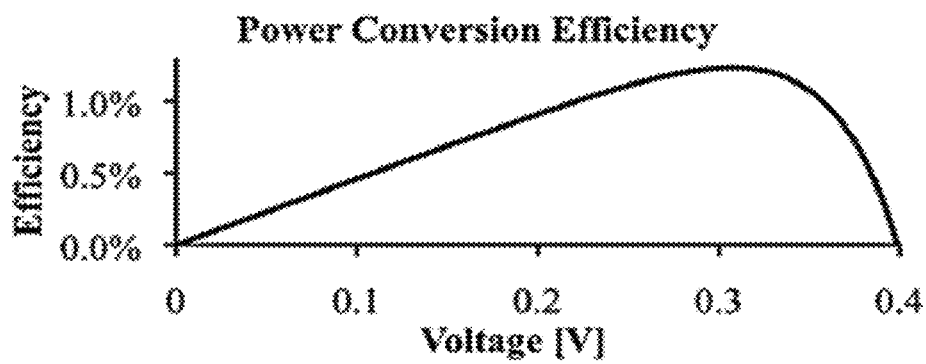
FIG. 9: Measured power conversion efficiency as a function of voltage at AM1.5 and 100 mW/cm$^2$.
Figure 10:
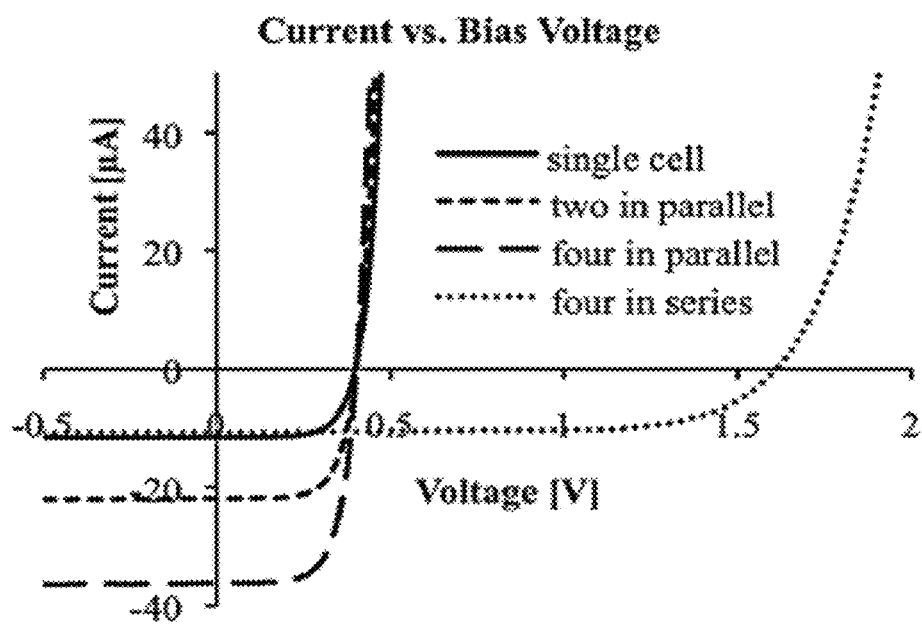
FIG. 10: Measured current vs. bias voltage of arrays of assembled micro solar cells at AM1.5 and 100 mW/cm$^2$.

FIGS. 7F and 7G schematically show the fabrication of a representative contact lens having a solar cell disposed thereon of the invention. A contact lens 816 is provided that comprises a substrate 802, which can be any material that can be used as a contact lens. Representative substrate materials include any of a number of materials including, but not limited to polymers and glasses. The contact lens 816 includes an electrical network that is patterned on the surface of the substrate 802, including an inner electrode 804, an outer electrode 806, and an interconnect network 811. The electrodes 804, 806 and the interconnect network 811 can all be deposited and/or patterned in the same lithographic step. The electrodes 804, 806 are electrically connected to, or integrated with, the interconnect network 811. The interconnect network 811 is illustrated as embedded below a passive (e.g., non-conducting) layer 807. In FIGS. 7F and 7G, the interconnect network 811 is illustrated as making electrical connection with electrode 806, although it will be appreciated that the interconnect network 811 may connect with either, or both of, electrodes 804 and 806. The interconnect network 811 may connect multiple devices 760 together and/or may connect the solar-cell device 760 to another electronic device on the contact lens 816 (not pictured) in need of electricity generated by the solar-cell device 760. For example, a radio-frequency transmitter. By including both a solar cell and an electronic device that can be powered by the solar cell on a contact lens, a powered contact lens is formed that needs no battery or other external power supply. The benefits of such a contact lens are numerous and include eliminating the need to change a battery on the contact lens, reducing waste (i.e., no batteries to dispose of), and reducing non-renewable energy consumption.

A means for attaching and electrically connecting components to the interconnect network 811 is applied to the electrodes 804, 806. In this representative embodiment, the attachment means is a solder. Solder 812 is deposited onto the metallic surfaces through wetting, as illustrated in FIG. 7F.

Preferably, the solder has a melting temperature of between about 40° C. and about 150° C.

The contact lens 816 is then placed in a fluid, heated to a temperature greater than the solder melting temperature, and solar cells 760 are introduced, as illustrated in FIG. 7F. Agitation may be used to facilitate the deposition into a recessed binding sites 814 on the contact lens 816. The recessed binding sites 814 can be formed, in one embodiment, by a passive material 808 (e.g., a photoresist) that defines the side-walls of the binding sites 814.

The shape of the solar cell 760 matches the shape of the recessed binding site 814 so as to facilitate the reception of the solar cell 760 into the recessed binding site 814.

Through agitation, capillary forces, gravitational forces, or mechanical forces, the solar cell 760 is received into the recessed binding sites 814 facilitated by the wetting effect and surface effects of the molten solder 812 interface with the electrodes 718 and 719. Non-electrode areas in the binding site 714 can be covered with a passivating layer 810, which confines the solder wetting to those metal surface where bonding is desired. The contact lens 816 is then cooled and the solder 812 solidifies, forming a mechanical and electrical contact between the electrodes 718, 719 of the solar cell 760 and the electrodes 804, 806 of the recessed binding site 814. The completed assembly 830 is illustrated in FIG. 7G.

An optional encapsulation layer 313 can be deposited (e.g., using spin-coating or other liquid-based techniques) over the assembly 830 to provide mechanical and/or chemical protection of the solar cell 760.

Fabrication, testing, and in vivo use of exemplary solar cells, including incorporation of the solar cells into contact lenses, are described below in Example 1 and FIGS. 8A-13.

Self-Powered Contact Lens with Glucose Sensor

It is noted in the above description of self-powered active contact lenses that one application of such a contact lens is monitoring glucose levels of the wearer. Such contact lenses are disclosed in the aspects and embodiments herein. Additionally, Example 2 is directed to such contact lenses.

In one aspect, a powered contact lens is provided. In one embodiment, the powered contact lens is formed from a transparent substrate shaped to be worn directly over a user's eye, the contact lens comprising:

(a) an annular antenna disposed at a margin of the contact lens, wherein the antenna is configured to both receive a power signal and transmit a data signal;

(b) a biosensor module configured to measure a characteristic of the user's eye, the biosensor module comprising and electrochemical sensor comprising:

(i) a working electrode;
(ii) a counter electrode;
(iii) a reference electrode; and
(iv) a biosensor circuit configured to measure the current across the working electrode and the counter electrode, to measure the voltage of the reference electrode, and to transmit a biosensor signal;

wherein the working electrode, the counter electrode, and the reference electrode are all configured to be in electronic communication when the contact lens is worn on the user's eye; and (c) a communications module configured to:
(i) process the power signal from the antenna to provide operational power to the biosensor module; and
(ii) process the biosensor signal to provide the data signal to the antenna.

In certain embodiments, the contact lens is powered by an antenna. In certain embodiments the antenna is an RF antenna formed from metal around the periphery of the substrate. An exemplary antenna is described further in Example 2 and comprises a 5 mm radius loop antenna made of gold line traces on the substrate. The antenna is configured to receive RF energy to power the contact lens (i.e., to power the glucose sensor and transmission hardware). The antenna is configured to receive RF signals in the 1-3 GHz range. The power received is about 5 µw or less, meaning that the sensor and transmission hardware must function within this power range.

In other embodiments, the contact lens is powered by a photovoltaic, as disclosed in previous aspects.

The contact lens includes a biosensor module. The biosensor module is configured to measure a biological characteristic of the user when the contact lens is worn on the user's eye. As disclosed herein, a representative biosensor is a glucose sensor. The tear fluid of the user is indicative of the glucose level of the user. Accordingly, measuring the glucose level of the tear fluid provides a measure of the glucose level of the user, without having to draw the user's blood, as in the predominantly used methods.

Figure 15A:
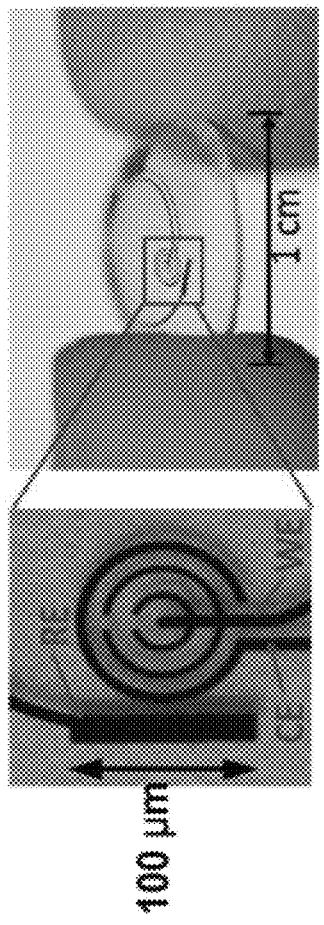
FIG. 15: 15A Design and 15B fabrication of glucose sensor.

The glucose sensor is an electrochemical sensor. The electrochemical sensor comprises three electrodes: A working electrode, a counter electrode, and a reference electrode, as illustrated in FIG. 15A.

While any electrochemical sensor can be used on the contact lens, in one embodiment, the working electrode comprises a plurality of concentric rings in electronic communication. In certain embodiments the counter electrode is annular in shape. In certain embodiments, the working electrode comprises a plurality of concentric rings in electronic communication, and the counter electrode is a concentric ring surrounding the working electrode.

The electrodes can be made of any materials known to those of skill in the art. Representative materials include one or more metals. In certain embodiments, a thin (e.g., less than 10 nm) adhesion layer of metal is applied to the substrate prior to depositing a thick (e.g. 50-500 nm) layer of a second metal. The three electrodes can have the same or different composition. In certain embodiments, at least one of the working electrode, the counter electrode, and the reference electrode comprises a metal stack of palladium intermediate titanium and platinum, wherein the stack is configured such that platinum is facing the user's eye.

To facilitate the basic electrochemical reaction for sensing glucose, a layer of the enzyme glucose oxidase (GOD) is combined with a titania sol-gel to form a membrane over exposed portions of the electrodes.

The biosensor module also comprises a biosensor circuit configured to measure and/or control the voltage of the working electrode, the counter electrode, and/or the reference electrode, and to transmit a biosensor signal. In one embodiment, the biosensor circuit regulates the voltages of the three electrodes and measures the current between the working and counter electrodes in view of the steady reference potential of the reference electrode.

The analog output of the biosensor circuit is transmitted to the communication module. It will be appreciated that the biosensor module and the biosensor module can be a single integrated circuit, or two separate integrated circuits connected by an interconnect (e.g., a metal interconnect).

The communication module operates both to process (e.g., transfer) power from the antenna to provide operational power for the biosensor and to perform the opposite operation: process the biosensor signal (e.g., analog output) to provide a data signal to the antenna for transmission.

In certain embodiments, the antenna used for powering the contact lens is used to transmit the data signal (e.g., by backscatter modulation). In other embodiments, a light-emitting diode (LED) is used to transmit the data signal, which can then be detected optically off-lens.

Both backscatter modulation communication techniques, as well as LED-based techniques for data transmission are described further in Example 2.

In another aspect, a powered contact lens is provided. In one embodiment, the powered contact lens is formed from a transparent substrate shaped to be worn directly over a user's eye, the contact lens comprising:

(a) an annular antenna disposed at a margin of the contact lens, wherein the antenna is configured to receive a power signal;

(b) a light-emitting diode (LED) configured to transmit a data signal;

(c) a biosensor module configured to measure a characteristic of the user's eye, the biosensor module comprising and electrochemical sensor comprising:

(i) a working electrode;

(ii) a counter electrode;

(iii) a reference electrode; and (iv) a biosensor circuit configured to measure the voltage of the working electrode, the counter electrode, and the reference electrode, and to transmit a biosensor signal;

wherein the working electrode, the counter electrode, and the reference electrode are all configured to be in electronic communication when the contact lens is worn on the user's eye; and (d) a communications module configured to:

(i) process the power signal from the antenna to provide operational power to the biosensor module; and (ii) process the biosensor signal to provide the data signal to the LED.

In another aspect, a powered contact lens is provided. In one embodiment, the powered contact lens is formed from a transparent substrate shaped to be worn directly over a user's eye, the contact lens comprising:

(a) a photovoltaic device disposed at a margin of the contact lens, wherein the photovoltaic device is configured to provide a power signal to the contact lens when exposed to electromagnetic radiation;

(b) a light-emitting diode (LED) configured to transmit a data signal;

(c) a biosensor module configured to measure a characteristic of the user's eye, the biosensor module comprising and electrochemical sensor comprising:

(i) a working electrode;

(ii) a counter electrode;

(iii) a reference electrode; and (iv) a biosensor circuit configured to measure the voltage of the working electrode, the counter electrode, and the reference electrode, and to transmit a biosensor signal;

wherein the working electrode, the counter electrode, and the reference electrode are all configured to be in electronic communication when the contact lens is worn on the user's eye; and (d) a communications module configured to:

(i) process the power signal from the photovoltaic device to provide operational power to the biosensor module; and (ii) process the biosensor signal to provide the data signal to the LED.

The following examples are intended to illustrate, and not limit, the embodiments disclosed herein.

EXAMPLES

Example 1

Fabrication and Testing of a Solar-Cell Powered Contact Lens

In this Example, we report the design, construction, characterization and in vivo testing of contact lenses incorporating solar cells. A fabrication process is outlined yielding free-standing 500×500×10 $\mu m^3$ single crystal silicon solar cells which are subsequently integrated into a contact lens. Collections of micron-scale solar cells are interconnected on the contact lens in order to maintain flexibility, cover the proper area, and take advantage of crystalline materials. The solar cells show maximum efficiency at wavelength 725 nm with conversion efficiency of 1.24% at 310 mV. The contact lenses were tested on live rabbits and no adverse effects were detected. Contact lenses equipped with solar cells can harvest usable power from the environment and pave the way for the deployment of stand-alone contact lens systems that can be used for information display or health-status monitoring.

Introduction

We propose that the ambient light provides such a power source for a contact lens system. Even indoors, on-lens solar cells could generate several microwatts to provide power for sensors, control circuitry, or solid-state memory, assuming ~0.5 $cm^2$ available area (i.e. contact lens area minus that of the pupil), ambient light of hundreds of $\mu W/cm^2$, and power conversion efficiency of a few percent.

Key steps in developing a contact lens with integrated photovoltaics are to fabricate miniature solar cells and to assemble them onto flexible polymer substrate forming contact lenses. We pursued this goal with two design constraints. The solar cells had to be: a) less than 1.0 $mm^2$ in area and less than 20 $\mu m$ thick to fit within the contact lens envelope, and b) compatible with our assembly processes that require coplanar electrical contacts.

The following sections report how we fabricated free-standing micro solar cells and integrated them onto contact lenses. We report the full characterization results of the devices and their in vivo test results.

Materials and Methods

Solar Cell Fabrication.

We fabricated solar cells using highly doped p-type SOI wafers to ensure ohmic metal contacts (Ultrasil Corporation, 0.01-0.02 Ohm-cm p-type, 10 $\mu m$ device thickness). First, we cleaned the wafers in 3:1 $H_2SO_4$:$H_2O_2$, 49% HF, and then 5:1:1 $H_2O$:HCl:$H_2O_2O$, with dump rinses in between. Then, 350 nm of wet thermal silicon dioxide was grown and patterned using a photoresist mask (MicroChemicals GmbH, AZ4620) and reactive-ion etching. The patterned silicon dioxide acted as a diffusion barrier for a spin-on-dopant phosphorus source (Filmtronics, Inc., P509), which created n-type emitters. We stripped the oxide and spin-on-dopant in 49% HF, and then created Cr/Ni/Au (15/50/200 nm, respectively) p and n electrical contacts using photolithography, electron beam metal evaporation, and a lift-off process. Cell widths and lengths (500 $\mu m$×500 $\mu m$ with chamfered corners) were defined using patterned photoresist (AZ4620) as a mask, and deep reactive-ion etching (DRIE) was used to isolate individual cells by etching device layer silicon down to the buried silicon dioxide (FIG. 7A). After stripping the photoresist with oxygen plasma in a barrel etcher, we spin coated polydimethylsiloxane (PDMS, Dow Corning Corporation, Sylgard 184 Silicon Elastomer Kit) on the processed SOI wafer and onto a bare silicon wafer. In order to minimize thickness variation caused by edge beads and etched trenches, we set the wafers on a flat surface and allowed the PDMS to planarize for several hours before curing overnight in a vacuum oven at 85° C. Next, both wafers were placed under low-power oxygen plasma for 30 seconds to prepare the surfaces for bonding. The wafers were immediately pressed together after the plasma treatment to bond the unprocessed and processed wafers (FIG. 7B). Using DRIE, we etched the entire back silicon thickness in the SOI handle wafer (FIG. 7C) and then etched the buried silicon dioxide using buffered oxide etchant (FIG. 7D). Lastly, we etched the PDMS in 3:1 n-methylpyrrolidone:tetrabutylammonium fluoride (Sigma-Aldrich Co LLC) and rinsed thoroughly in deionized water, resulting in a collection of freestanding micro solar cells (FIG. 7E).

Micro Solar Cell Assembly on Contact Lens.

Contact lenses and polymer test templates with metal interconnects and pads for solar cells were fabricated on optically transparent wafers of polyethylene terephthalate (PET) cut from 24.5 cm×24.5 cm sheets using a $CO_2$ laser. We used photolithography, metal evaporation, and a lift-off process to create Cr/Ni/Au (15/80/200 nm) electrical pads and interconnects and then deposited and patterned a thin, transparent polymer layer (SU-8 2) for electrical insulation and to restrict solder wetting (SU-8 2, MicroChem. Corp.). A thicker (~25 µm) transparent photoresist (SU-8 25, MicroChem. Corp.) was patterned to create micro wells into which solar cells could be roughly aligned. In order to ensure overlap of template and solar cell solder pads during assembly, wells were designed to be one solder pad width wider than a solar cell in each direction (in this case 80 µm). Lastly, we cut contact lens-sized discs from the wafer, again using a $CO_2$ laser.

Prior to assembly, the exposed template pads were coated with low melting temperature solder alloy (Indalloy 19, Indium Corp.). The solder was placed in a beaker and covered with ethylene glycol (EG) and then heated on a hotplate in a bath of boiling water to maintain a constant temperature of approximately 95° C. Once the solder melted, 65 µL of HCl was added to the EG to remove surface oxidation and contamination. Subsequently, the clean solder was dripped onto the template using a pipette, wetting all exposed metal.

Two assembly methods were used without observable differences in performance. In the first method, the freshly coated templates were submersed in a solution of 25 mL of EG and 10 µL of HCl in a petri dish and the solar cells were placed in the SU-8 25 wells using a pipette under a microscope. After the solar cells were positioned, the solution was heated, facilitating solder reflow that provided fine alignment in addition to mechanical and electrical connection between the cells and template. Cells "snapping" into alignment provided visual indication of successful assembly. In the second method, the templates were cleaned with isopropyl alcohol (IPA) and dried with nitrogen immediately prior to assembly, and micro solar cells were roughly placed using a flip chip placement machine (Finetech Corp, Fineplacer Pico). After placement, the templates with cells were carefully submerged in the EG/HCl solution and allowed to reflow in the manner described above.

After assembling and cleaning in IPA, we tested individual cells and four-cell arrays. Additionally, we assembled larger arrays on planar discs laser cut from PET wafers. Polymer discs with assembled cells were molded into contact lenses at 200° C. on an aluminum mold with appropriate curvature for rabbit corneas (7.1 mm). Then we conformally deposited ~10 µm of parylene-C (PDS 2010 Labcoater® 2, Specialty Coating Systems) on the molded lenses to protect solar cells, provide biocompatibility, and increase durability. Prior to rabbit testing, the molded lenses were cleaned in oxygen plasma and sterilized in ethanol.

Results

We fabricated and assembled 500×500×10 µm³ solar cells from p-type SOI wafers, as shown in FIGS. 8A-8D. Detailed fabrication and assembly procedures are described above.

Solar cell performance was determined using an Oriel solar simulator comprising a xenon lamp coupled to an AM1.5 filter, calibrated to 100 mW/cm² using a Hamamatsu S1787-12 photodiode. Maximum power conversion efficiency of 1.24% was measured at 310 mV (FIG. 9), with a fill factor of 0.67. The mean short circuit current was 11.5 µA with 1.8 µA standard deviation. We also tested series and parallel configurations of assembled solar cell arrays using the same illumination, the result of which can be seen in FIG. 10. Using series and parallel configurations allows us to create application dependent voltages and currents.

Figure 11:
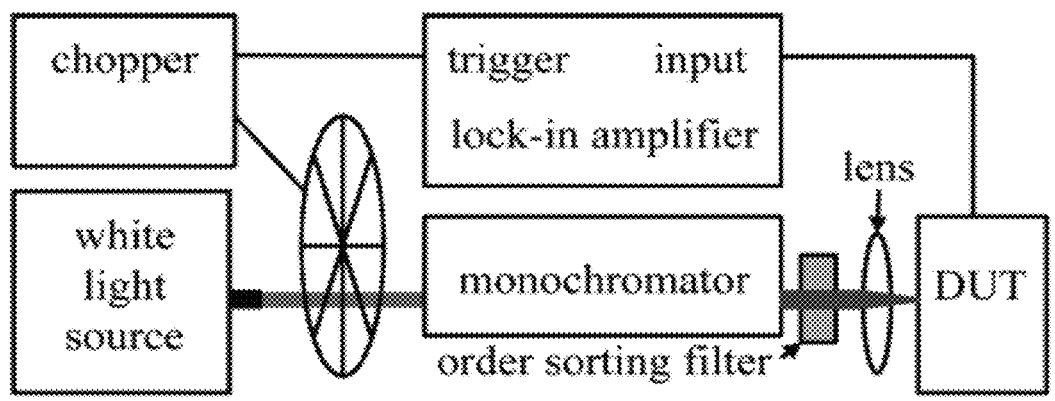
FIG. 11: Setup to measure responsivity as a function of wavelength. White light passes through a chopper and into a monochromator. The narrowband output passes through an order-sorting filter and is focused onto a device-under-test (DUT). DUT short circuit current is measured using a lock-in amplifier that is triggered by the chopper. Measurements were taken from 400 nm to 1100 nm.

Solar cell responsivity was measured using the setup depicted in FIG. 11. White light from an Oriel 77501 source passes through a chopper (Stanford Research Systems, Inc., Model SRS40) operating at 100 Hz and then into a Czerny-Turner-type monochromator (Action Research Corporation, SpectraPro-275). The narrowband output is focused onto a photovoltaic device under test (DUT). The DUT is connected to a lock-in amplifier (Stanford Research Systems, Inc., Model SR810 DSP Lock-In Amp) that is triggered at the chopper frequency. To ensure that we eliminated overlapping orders from the monochromator diffraction grating, we used an order-sorting filter with a cutoff wavelength of 530 nm when measuring 525 nm and above. Thus, two scans were performed each device under test: one ranging from 400 nm to 600 nm without an order-sorting filter, and a second filtered from 525 nm to 1100 nm.

Figure 12:
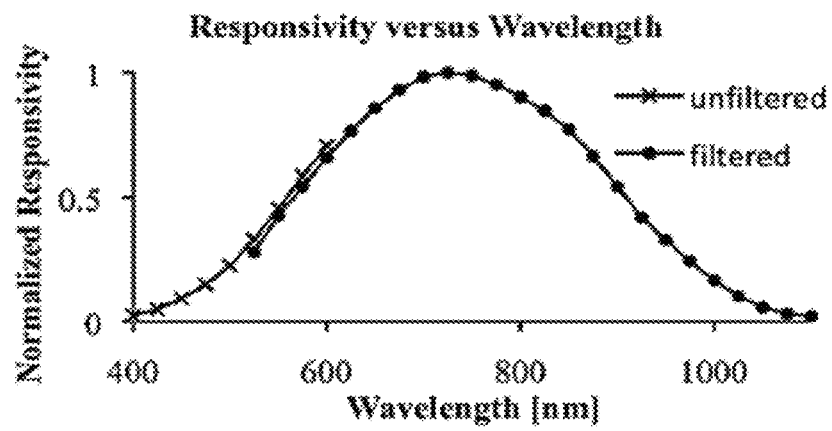
FIG. 12: Normalized measured micro solar cell responsivity. Peak responsivity occurs at approximately 725 nm; shorter wavelength light absorbs near the surface, far from the depletion region, and longer wavelength radiation passes through the cell.

First, we measured the short circuit current ($I_{sc}$, [A]) of a known photodetector (Newport Corporation, 818-SL) at wavelengths from 400 nm to 1100 nm at 25 nm intervals and divided by the corresponding calibrated responsivity [A/W] to determine light source power [W]. Next, $I_{sc}$ was determined for several assembled solar cells using the same experimental setup. Due to their small size, each cell was mounted on a three axis micro positioner and translated until $I_{sc}$ maximum was reached. Finally, solar cell responsivity was calculated by dividing measured $I_{sc}$ [A] by the previously determined optical power [W] and then normalized (FIG. 12).

Figure 13:
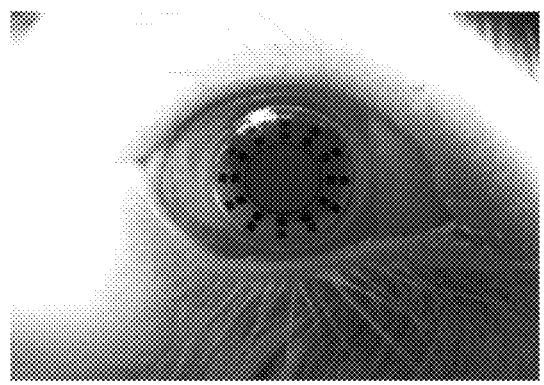
FIG. 13: Image of a contact lens with a 2×12 solar cell array placed on live rabbit eye.

In preparation for further testing of complete contact lens systems with embedded sensors and circuitry, we molded and parylene coated a 2×12 array (2 cells in a radially aligned pair, and 12 radially aligned pairs spaced around the circumference of the lens) of solar cells to build a contact lens for in vivo fitting in a rabbit. Experiments were conducted under general anesthesia in the University of Washington vivarium, under the guidelines of the National Institutes of Health for use of laboratory animals, with the approval of the Institute of Animal Care and Use Committee of the University of Washington (Protocol #UW4139-01). Female New Zealand White Rabbits (mean wt. 2.5 kg) underwent general anesthesia with 5% induction of isoflurane and oxygen, which were maintained at 2% during the in vivo studies. Artificial tears were applied frequently to ensure corneal hydration. The prototype contact lens was well-fitted on the rabbit ocular surface (FIG. 13). We evaluated the effects of the contact lens on the rabbit cornea using portable slit lamp biomicroscopy and corneal pachymetry. Topical fluorescein was applied to the corneal surface, and the rabbit was evaluated for potential corneal abrasion or corneal edema as a result of the in vivo testing. No adverse effects were observed as a result of the contact lens wear.

Discussion

In back-junction solar cells, there is often a tradeoff between maximum light absorption and diffusion of free carriers to the depletion region. If cell thickness is large compared to absorption depth, free carriers created near the surface will not diffuse to the depletion region or contribute to power generation. Conversely, if the cell is too thin, light can pass directly through the cell without being absorbed. This tradeoff is observed in our cells, with optimal responsivity occurring near 725 nm. This corresponds to an absorption depth of about 5 μm, which is close to the depletion region depth. Although responsivity can be dependent on incident optical power, which was not constant over the light source spectra, our results correlate well with other crystalline silicon cells of similar thickness.

Although the efficiency of our cells is lower than that reported for some of the other crystalline silicon cells of small size, we reached our goal of mass producing micron scale cells and successfully integrating them into a biocompatible contact lens. We aimed to simplify processes as much as possible in order to enable cost-effective mass production of these devices. The cell design described herein is based on a single diffusion and one metallization and did not include surface passivation, back surface reflectors, surface texturing, or anti-reflection coatings. Additionally, cell geometry was determined with emphasis on size constraints and mechanical stability required for use in contact lenses rather than on energy conversion efficiency optimization.

A contact lens that can mainly operate based on the optical power harvested from the environment, can collect biomarker information from the surface of the eye, and can wirelessly report the results will fundamentally change healthcare by enabling a non-invasive and disposable system that can continuously interface with the human body.

Example 2

Self-Powered Contact Lens with Glucose Sensor

Figure 14:
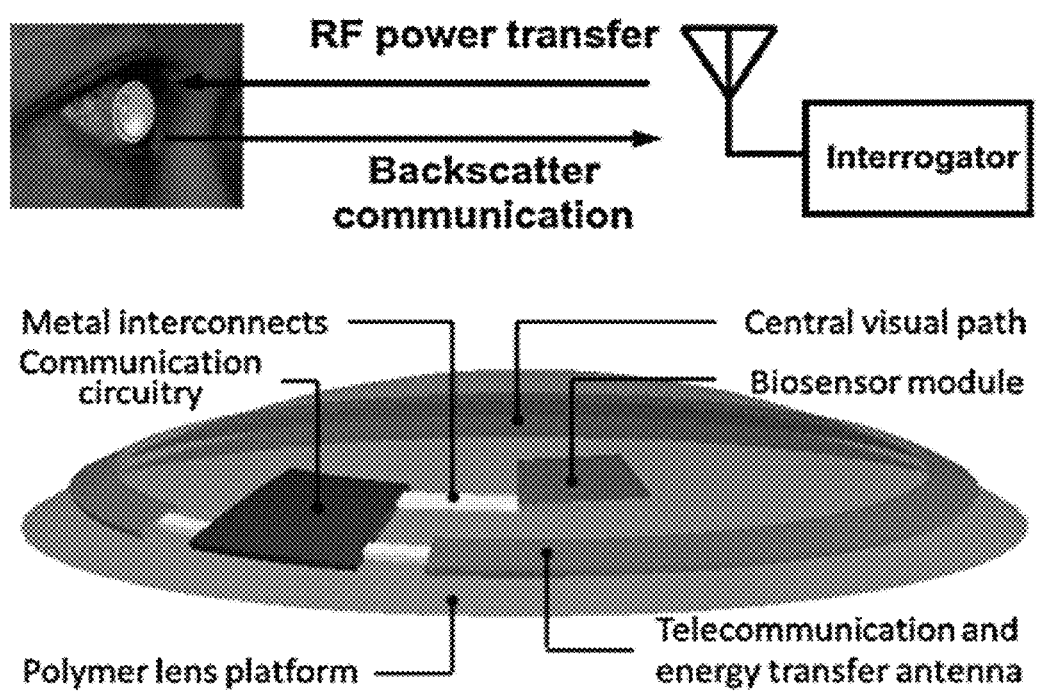
FIG. 14: Conceptual diagram of an active contact-lens system for wireless health monitoring.

Disclosed herein is a fully integrated active contact lens system for wirelessly and continuously monitoring glucose levels. The on-lens electrochemical sensor provides real-time continuous glucose monitoring and high sensitivity compared with conventional glucose monitoring. The sensor directly accesses the tear fluid and thus can improve the sensitivity and reduce the sampling processes and potential of infection during operation. FIG. 14 shows the conceptual diagram of wireless health monitoring using an active contact lens. The active contact lens system includes a glucose sensor, an antenna, a communication interface, and readout circuitry, all on a polymer lens substrate. The on-lens glucose sensor system detects the tear glucose level and then wirelessly transmits the information to an external reader. This system is useful, for example, as a point-of-care device in tandem with the near-field communication feature of mobile phones.

There are many challenges in the implementation of the on-lens sensor system. First, the system is extremely constrained by power and area. A standard contact lens has an area of about 1 cm² and a total thickness of about 200 μm. Component size in the design is severely restricted, roughly 0.6×0.6 mm², which is determined by the curvature of the eye and our assembly process. Clearly, standard surface-mount components are too large for integration onto a contact lens. In addition, volume limitations eliminate the possibility of large energy storage devices. Therefore, a biosensor on a contact lens must be powered wirelessly through external sources (e.g., RF power, inductive power, or optical power). Third, the active contact lens system requires the heterogeneous biocompatible integration of different devices/materials on a plastic substrate. Finally, possible issues of using the sensors on the eye may include RF-power-caused eye temperature increase, vision-blocking, and damage from on-lens device. The regulation of RF-power-caused temperature rises is still under study for human eyes. We have adhered to the IEEE C95 standard to minimize risk in this area. To reduce the intrusion and damage of devices, on-lens devices can be embedded into the lens. The devices on the contact lens are out of the focus of human eyes and are placed in the outer of a lens to further avoid vision blurring.

Design and Fabrication of the Glucose Sensor

Compared with traditional analytical techniques, electrochemical methods, based on oxidizing or reducing the target analytes, can achieve a real-time, quick-response, high-efficiency, and cost-effective analysis. The electrochemical reaction of an enzyme-based glucose sensor can be expressed as:

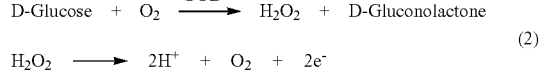

$$\text{D-Glucose} + \text{O}_2 \xrightarrow{\text{GOD}} \text{H}_2\text{O}_2 + \text{D-Gluconolactone} \quad (1)$$

$$\text{H}_2\text{O}_2 \longrightarrow 2\text{H}^+ + \text{O}_2 + 2e^- \quad (2)$$

The basic electrochemical reaction for sensing glucose starts from catalyzing glucose to hydrogen peroxide ($H_2O_2$) using the enzyme glucose oxidase (GOD). $H_2O_2$ is further oxidized at the electrode to release electrons, generating a current signal proportional to the glucose concentration.

A. Glucose Sensor Design and Fabrication

Figure 15B:
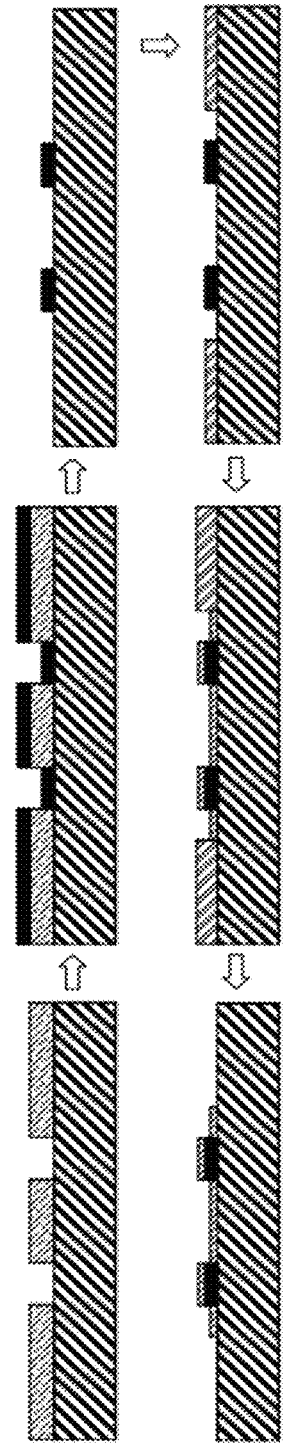

To make a stable electrochemical sensor, three electrodes are typically used: a working electrode (WE) where the target analytes are involved in an oxidation or reduction process, a counter electrode (CE) (also known as an auxiliary electrode) operating as a current drain to make an electron loop, and a reference electrode (RE) that provides a stable voltage potential for the whole system. In the disclosed sensor [FIG. 15A], the working and counter electrodes are designed as concentric rings with widths of 50 and 75 μm, respectively), which have a 50-μm pitch to decrease the resistance and thus enhance the sensor sensitivity. The reference electrode is designed as a rectangular bar 1.6 mm×0.25 mm) close to the sensing area. FIG. 15B shows the fabrication process of glucose sensor. The fabrication starts from a transparent polyethylene terephthalate (PET) polymer film (100-μm thickness). Three metal layers, Ti, Pd, and Pt, are evaporated in sequence to achieve thicknesses of 10, 20, and 100 nm, respectively, to create electrodes. Then, the exposed Ti/Pd/Pt sensor surface is pretreated with a GOD/titania sol-gel membrane. The detailed fabrication and pretreatment process is reported in H. Yao et al., "A contact lens with embedded sensor for monitoring tear glucose level," *Biosensors Bioelectron.*, 26(7):3290-3296, 2011.

B. Sensor Calibration

Figure 16:
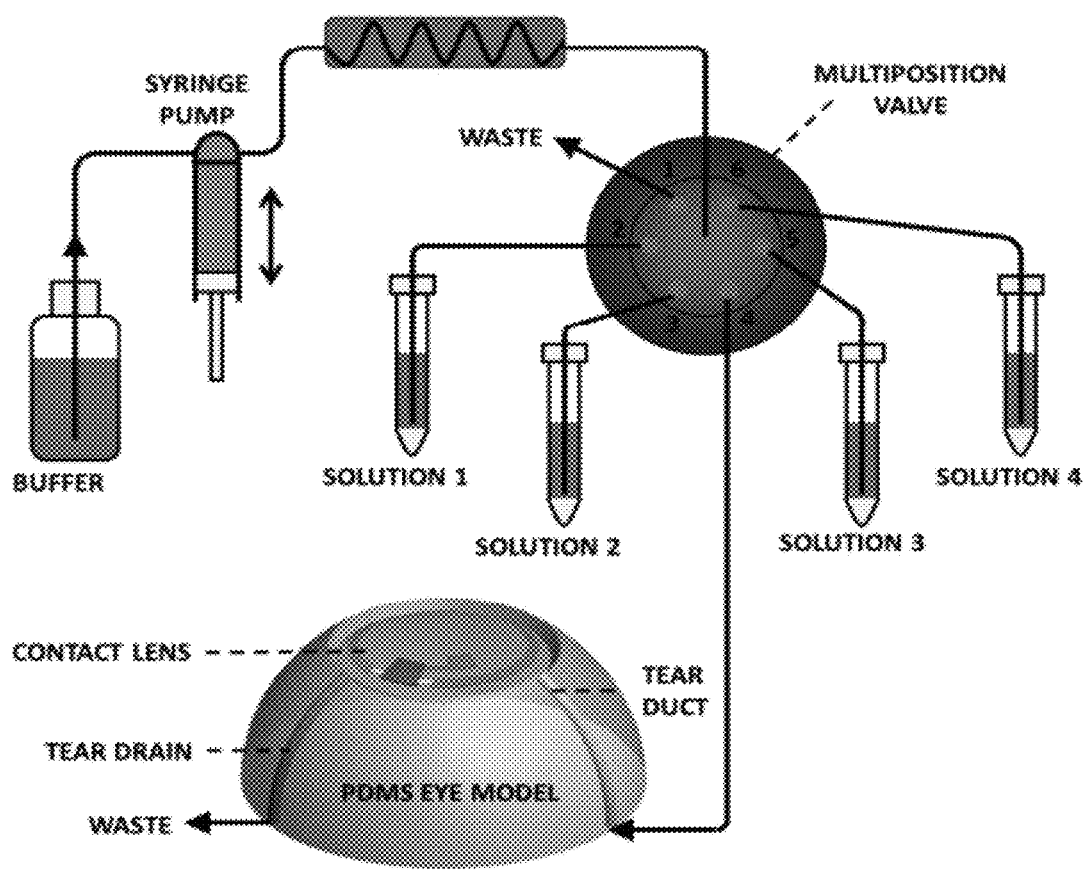
FIG. 16: Measurement setup of continuous flow test.
Figure 17:
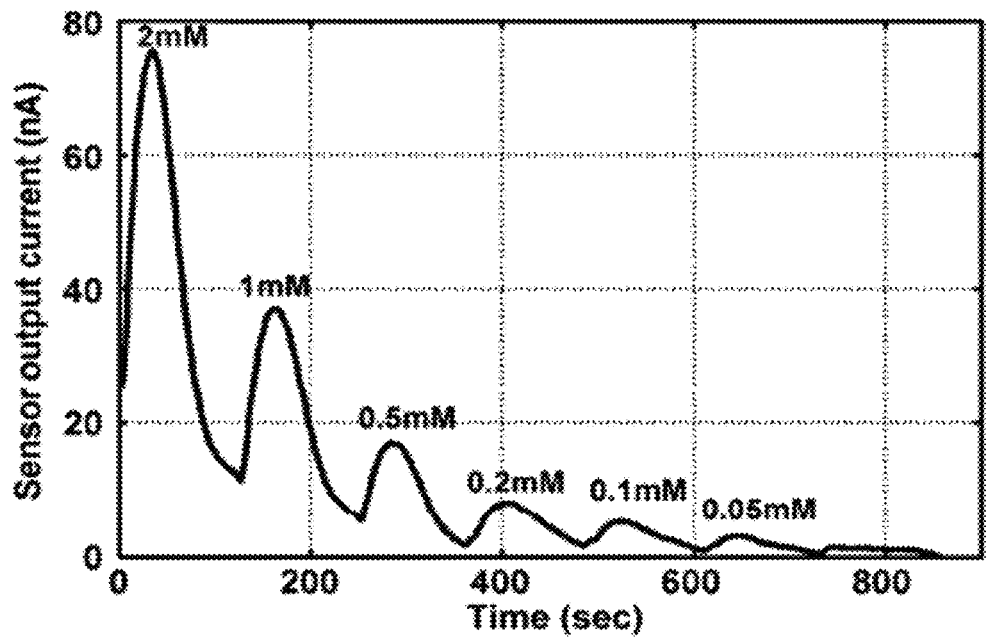
FIG. 17: Measured sensor response of continuous glucose flow.

We designed and fabricated a polydimethylsiloxane (PDMS) eye model mimicking a human eye to test the sensor in a continuous microfluidic system, as shown in FIG. 16. A FI-Alab-3000 fluidic analyzer (6 multi-position valves) is applied to continuously deliver different solutions into the tear duct, and another syringe pump aspirates at the same flow rate from the tear drain. The sensor was tested using the PDMS eye model, which more closely resembles an on-eye scenario than beaker testing. FIG. 17 shows measured results of continuous glucose flow tests. The average response time to reach the maximum value in the continuous flow setup is about 35 s, including 15 s for the pump to deliver the test solution to the eye model and sensor response time of 20 s.

Figure 18:
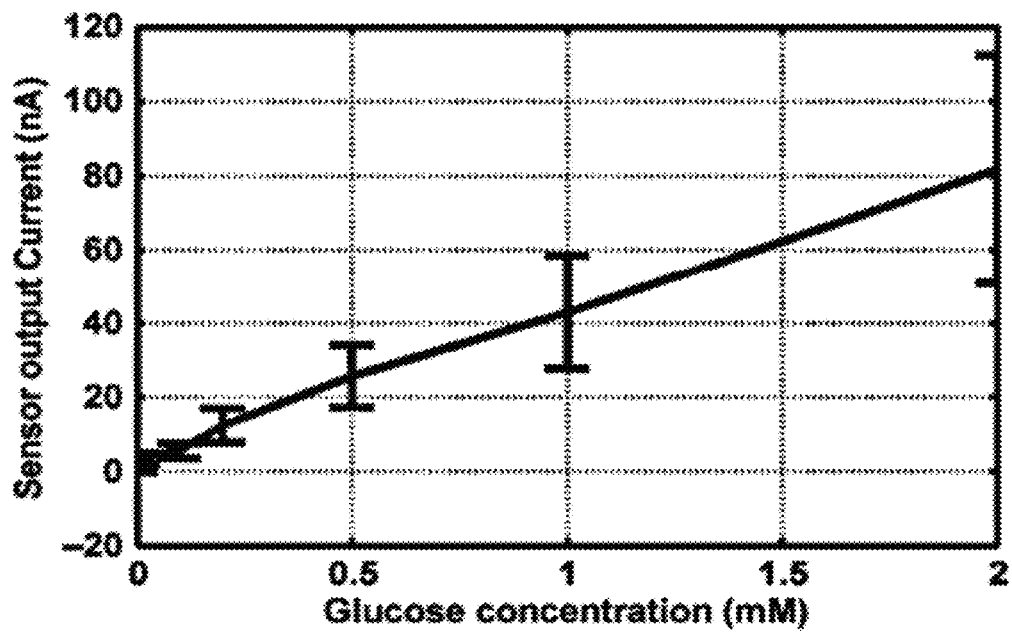
FIG. 18: Measurement results of sensor output current versus glucose concentration.

The linearity curve (FIG. 18) is generated by collecting the current peak response from five independent sensors. Normal glucose levels in human tear film are roughly 0.1-0.6 mM. The usable glucose concentration range of the proposed sensor is 0.05-2 mM, which safely covers the relevant human range. The electrochemical current generated is around 1-20 nA in the glucose levels relevant for human tear sensing. The sensitivity of our glucose sensor is $0.18 \ \mu A \cdot mm^{-2} \cdot mM^{-1}$. In this sensor design, a layer of Nafion used previously to improve the sensitivity and the interference rejection was removed since Nafion promotes random protein absorption due to eventual foreign body encapsulation. The measurement discrepancies among these five sensors mainly result from the different surface circumstance and enzyme immobilization of the sensors, which are caused by the manual microfabrication processes.

Wireless Readout Chip Architecture

Figure 19:
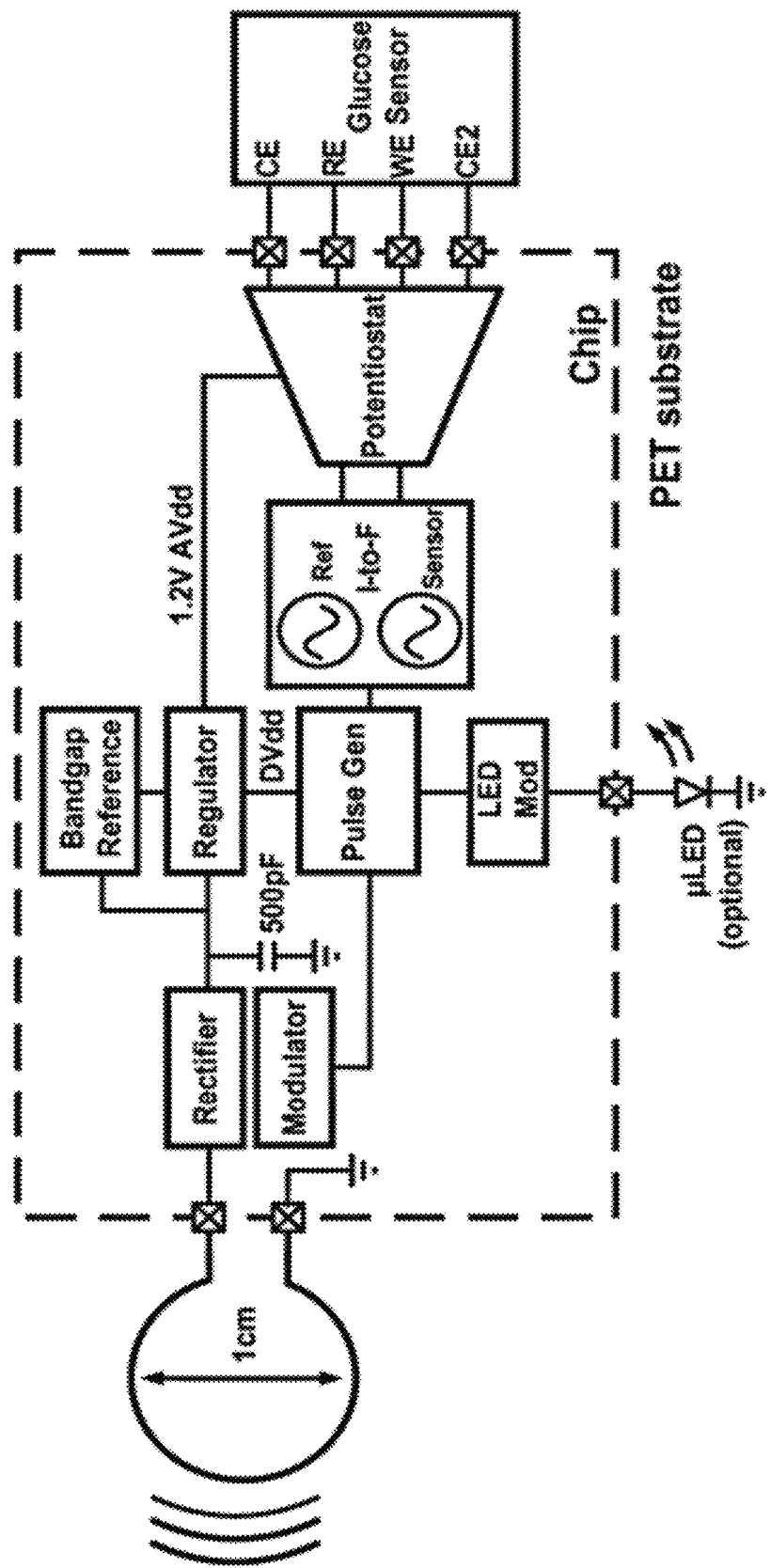
FIG. 19: System architecture of the readout IC.

The goal of the on-lens sensor readout system was to implement a low-power (<5 $\mu$W), low-current-noise (<1 nA rms) design in a severely constrained area (0.36 mm$^2$). FIG. 19 shows a representative sensor readout architecture. The IC consists of a power management block, readout circuitry, wireless communication interface, LED driver, and energy storage capacitors in a 0.36 mm$^2$ CMOS chip with no external components (e.g., quartz crystals, inductors, capacitors, or batteries). The system is wirelessly powered using RF power sent from an interrogator. The challenges in making an integrated RF power-harvesting system include designing an efficient rectifier, low-power voltage reference/regulator, and a sufficiently large on-chip storage/filtering capacitor. These challenges are greatly exacerbated by the fact that large value high-Q surface-mount passives and an efficient antenna cannot be used.

In addition, accurate detection of the low sensor current requires stable supply voltage, reference voltages, and low-noise electronics. To reduce the supply fluctuation caused by varying strength of incident RF power and digital switching noise, we designed an ultralow-power linear regulator, bandgap reference, and bias current generation, which provide stable bias and supply for the chip. The low-noise readout electronics include a potentiostat to enforce a stable potential between WE and CE to start the oxidation reaction. The CE2 node can be connected to a reference sensor for biochemical interference rejection. The sensor current is amplified and then injected into an oscillator-based current-to-frequency (I-F) converter that directly encodes the sensor current as a modulated tone. Finally, the 0.36 mm$^2$ system wirelessly communicates with the interrogator through RF backscatter (by either absorbing or reflecting the carrier signal sent by the interrogator).

Circuit Implementation

A. Antenna Design

Figure 20:
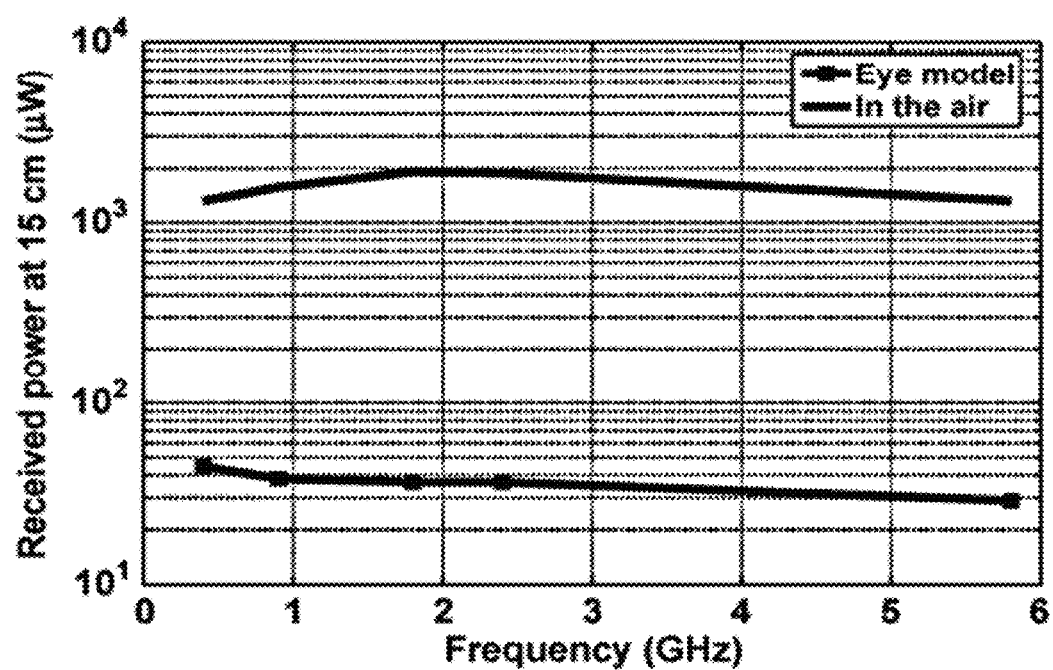
FIG. 20: Simulated results of received power in the air and on the eye model (transmit power=1 W at a 15-cm distance).

The design of the antenna is severely constrained by the required contact lens size, flexibility, and transparency. A 5-mm-radius loop antenna is used to receive RF energy without obstructing wearer vision. For an on-lens system, surface mount parts are prohibitively large, so the chip and antenna must be directly connected without an external matching network. The impedance matching between chip and antenna is absorbed into the antenna design. The loop antenna was designed and fabricated using gold traces on a PET substrate. To determine power received by the on-lens antenna, we simulated the gain for a loop antenna with a 5-mm radius, 0.5-mm trace width, and 5-$\mu$m thickness. The received power is calculated using the Friis transmission equation, assuming perfect antenna-chip matching and minimum transmit antenna gain (1.76 dBi for a dipole antenna). FIG. 20 shows the results of received power in the air and on an eye model (tear film, cornea, aqueous humor, and vitreous humor) at a distance of 15 cm from an isotropic transmitter (1-W output power). At low frequency, the received power is limited by the efficiency of the antenna; at high frequency, the path loss dominates the received power. An optimal frequency exists between 1.5-2.5 GHz for our size-constrained antenna design in free-space communication. The simulated antenna gain on the eye model in the direction of the transmitter (perpendicular to the plane of the loop antenna) is 17 dB lower than the antenna gain in air in the 1.8 GHz ISM band, giving about 20 $\mu$W received power. Therefore, the maximum power consumption of readout electronics should be less than 5 $\mu$W (assuming 25% power transfer) to provide a reasonable communication distance.

B. Power Delivery and Rectifier Design

The on-chip power management circuits comprise a full-wave rectifier to convert RF power to a dc voltage and a low power regulator to provide a stable 1.2-V voltage supply, which is subsequently filtered by a 500-pF on-chip capacitance. The rectifier is built using a five-stage Dickson full-wave architecture. Low-Vth pMOS transistors with the body terminal tied to the source are employed to eliminate the body effect and enhance sensitivity by reducing the turn-on voltage of transistors. The simulated peak power efficiency of the rectifier is about 20%.

C. Regulator and Bias Generation

Figure 21:
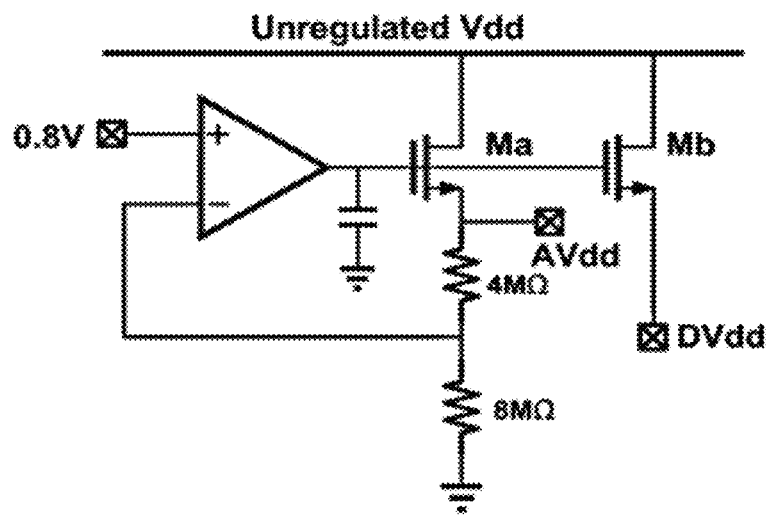
FIG. 21: Schematic of on-chip regulator.
Figure 22:
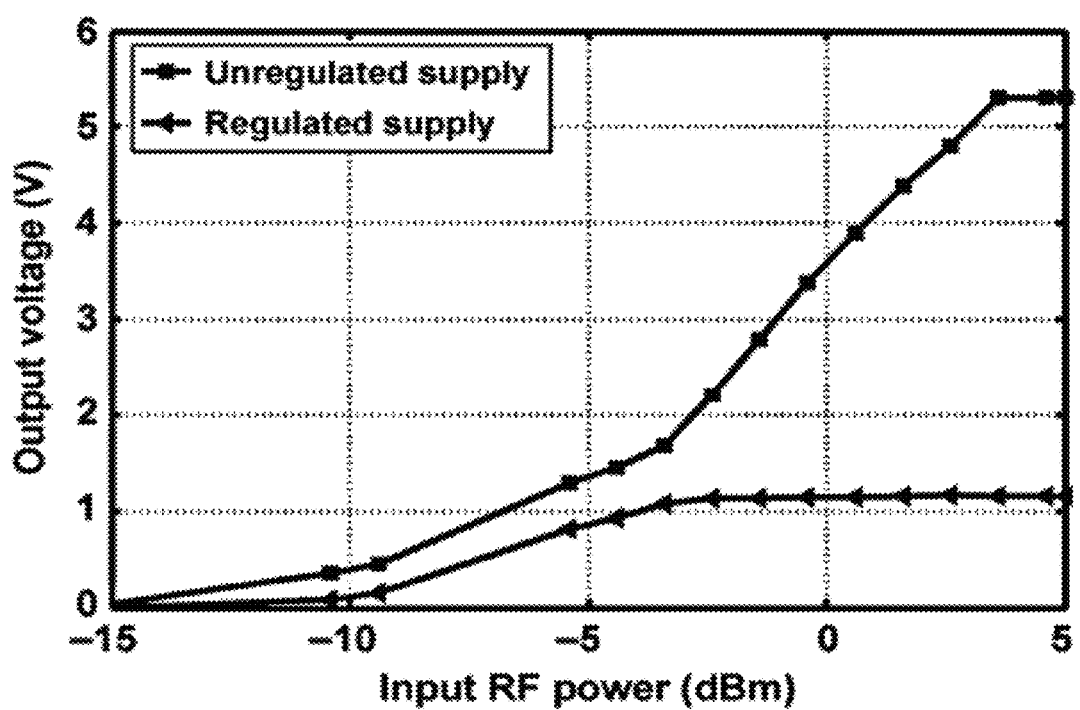
FIG. 22: Measured output voltage of regulated and unregulated supplies (An on-chip clamp limits voltage to 5 V.)

Two major problems of an RF-powered wireless sensor system are the supply fluctuation due to the varying incident RF power and supply noise due to the fast switching of digital circuits. First, to reduce supply variations, a low-power regulator with bandgap reference was employed, providing a clean and temperature-stable 1.2-V supply to the entire system. A large filtering capacitor is desired to reduce high-frequency supply noise and large voltage drops. To reduce area, the on-chip capacitor is stacked vertically with dual metal-insulator-metal (MIM) capacitors and metal finger capacitors using the middle four metal layers and MOS capacitors. An on-chip capacitance of 500 pF is implemented in an area of ~0.2 mm$^2$. Second, a separate digital and analog supply regulation technique is employed to reduce noise coupling into the sensing element (sensor and readout circuitry) from the oscillator as well as logic switching noise. The schematic of the regulator is shown in FIG. 21. To provide isolation between digital and analog supplies without adding an extra regulator, the regulator pass transistors are separated. This topology achieves 30-dB isolation between digital and analog supply while consuming 500 nW. The low-power bias circuit and amplifier design is described in more detail in D. Yeager, et al., "A 9 mu a, Addressable Gen2 Sensor Tag for Biosignal Acquisition," *IEEE J. Solid-State Circuits*, 45(10): pp. 2198-2209, October 2010. FIG. 22 shows the measured output unregulated/regulated voltage versus swept input RF power.

D. Potentiostat

For electrical current measurement, a transimpedance amplifier is a popular approach that measures low current levels by using high measurement resistance. However, the transimpedance amplifier configuration usually has an inductive input impedance, which may cause instability in the potential control loop due to the large and varying capacitive components of an in-eye electrochemical cell. To accommodate high uncertainty in the sensor capacitance, a current mirror-based topology was used to copy and measure the sensor current.

Figure 23:
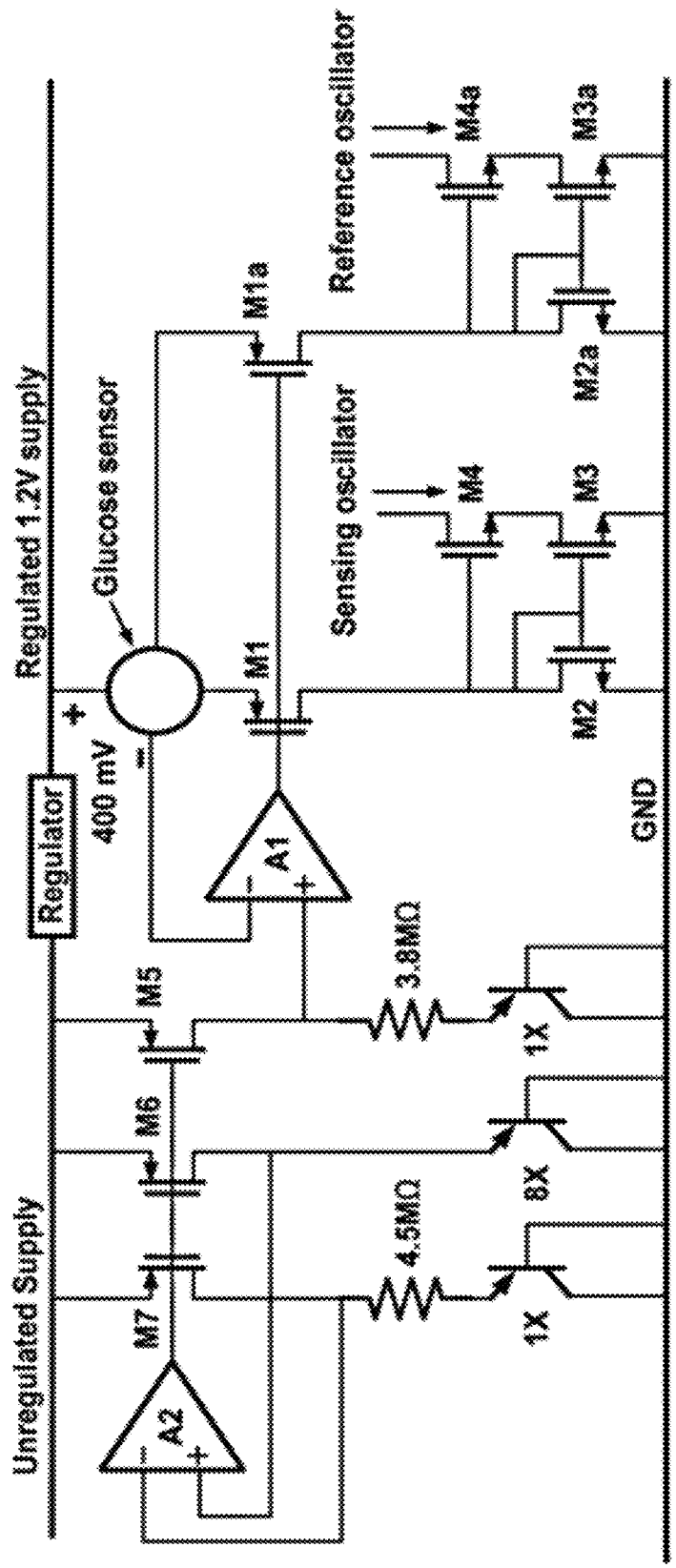
FIG. 23: Schematic of a potentiostat (this circuit enforces a 400-mV potential across the glucose sensor while reading out the resulting nA-level current.)

FIG. 23 shows the schematic of proposed readout circuitry. The voltage control loop, consisting of a bandgap reference, amplifier (A1) and a pass transistor (M1), provides a stable potential of 400 mV between the working and counter electrodes. The choice of a 400-mV potential achieves the optimal signal-to-noise ratio (output current/background noise) as given by previous measured results of our glucose sensor. A frequency-compensation capacitor is added at the output of feedback amplifier to stabilize the potential control loop. The sensor current is mirrored with a cascode topology that improves the precision of current replication.

E. Current-to-Frequency Converter

Figure 24:
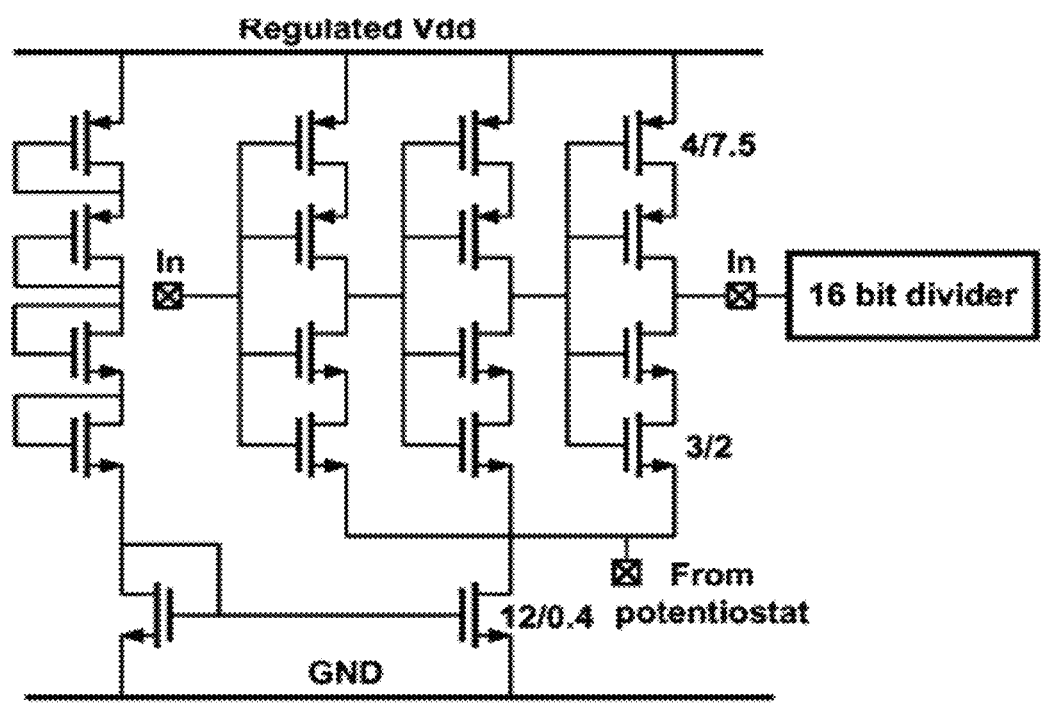
FIG. 24: Schematic of I-F converter.
Figure 25A:
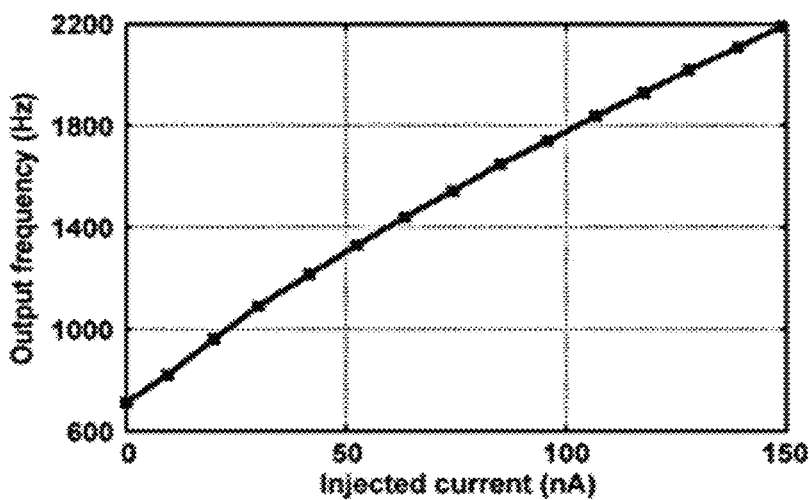
FIG. 25: Measured output frequency versus 25A injected current, 25B supply voltage, and 25C temperature.

A ring oscillator-based current-to-frequency (I-F) converter (FIG. 24) directly converts the sensor current signal into a rail-to-rail digital output without an explicit ADC. This saves area, power, and complexity. The oscillator normally operates at 350 kHz and consumes 300 nA. The output frequencies of the reference and sensor oscillator are divided down to reduce high frequency noise/instability. The sensor current is injected into an oscillator-based I-F converter. The oscillation frequency of a current-starved ring oscillator can be expressed as $$f_{osc} = \frac{I_d}{N \cdot C_{tot} \cdot V_{dd}} \quad (3)$$

where $I_d$ is the current of each stage, N is the number of stages, $V_{dd}$ is the supply voltage, and $C_{tot}$ is capacitance at the output of each stage. The oscillator frequency shifts proportionally to the injected sensor current. FIG. 25A shows the measured output frequency (after dividing by 512) versus sweep injected current. The I-F converter achieves a gain of 9.9 Hz/nA.

Figure 25B:
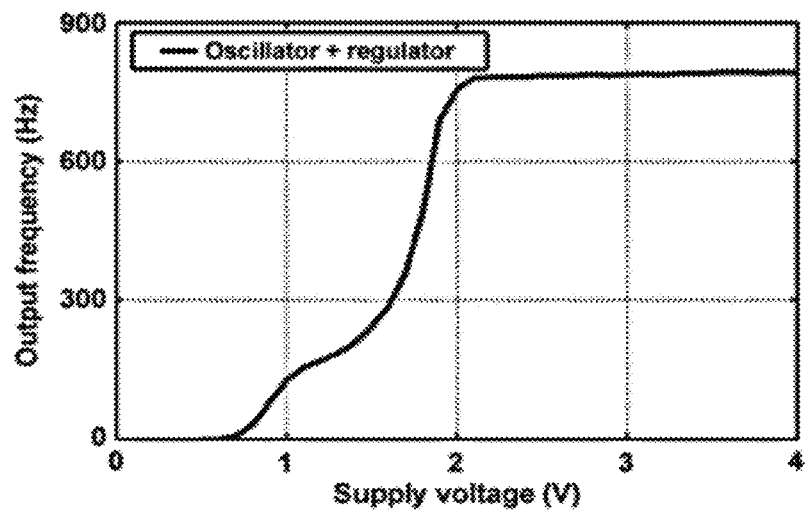
Figure 25C:
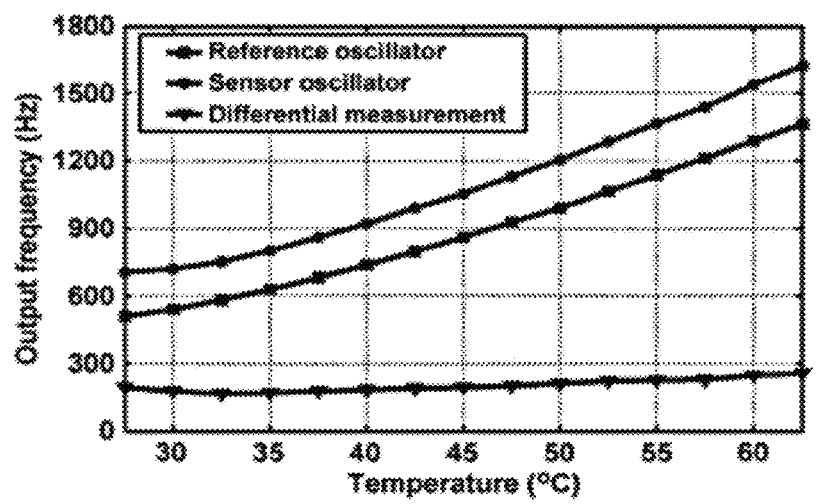

The process, voltage, and temperature variations of the ring oscillator are reduced by using large devices and careful layout, a regulated voltage supply, and differential measurement using a reference oscillator and the sensing oscillator. FIGS. 25B and 25C shows the measured output frequency (divided by 512) of the I-F converter versus supply voltage and temperature, respectively. The temperature coefficient of the I-F converter is 20 Hz/° C. from 30° C. to 60° C. and can be effectively reduced to 2.6 Hz/° C. by subtracting the result of the reference oscillator from the result of sensor oscillator.

F. Pulse Generator and Backscatter Modulator

To wirelessly read out sensor data, backscatter communication is adopted in our system. Backscatter modulation is attractive for active contact lens applications because it allows for a nearly zero power lens-to-reader communication. Since the body glucose level changes slowly, it is not necessary to store/transmit data frequently. However, there is a tradeoff between power delivery and backscatter signal strength. A strong backscatter signal may cause large supply voltage drops, which can be problematic in our system due to small energy storage capacitance on the chip and the low tolerable supply ripple. Therefore, a pulse generator is integrated to allow a low duty cycle (10%) modulation signal to achieve a reasonable compromise between supply voltage droop and backscatter strength.

FIG. 26A shows the schematic of pulse modulators. The divided signals from the fifth and ninth bits of a 16-bit divider chain are used to create the pulses. The pulsewidth equals the period of the reference oscillator and the pulse period is twice the period of sensor oscillator. Using this technique, frequency information from both the sensor and reference oscillator are simultaneously transmitted to the interrogator and can be decoded in the reader. A single transistor switch is used to modulate the reflection coefficient. A 3.3-V-thick oxide device and a diode-connected voltage limiter are used to prevent breakdown when the system is placed near the reader.

An alternative method of wireless communication is to slowly modulate an on-lens µLED for immediate visual feedback to the contact lens wearer. The µLED design and fabrication is shown in our previous work. Since lighting a customized µLED consumes much more power (~70 µW at 2.5 V for visible light) than the sensor, we duty-cycled the LED to save power. FIG. 26B shows the pulse generators used for optical detection. The frequency of the reference signal is divided down to 4 Hz with the 16-b counter. The LED is lit in the first half period to transmit data and turned off in the second half period to conserve energy. A pulse generator that drives the LED creates a narrow pulsewidth (~3 µs to reduce LED on-time and effectively lower the LED power consumption. The number of pulses in an on-cycle represents the frequency difference between reference oscillators and sensor oscillator, which corresponds to the glucose concentration.

System Assembly

Here, we describe the on-lens integration of the sensor, IC, and antenna. First, we cut 100-mm wafers from PET films and cleaned them with acetone, isopropyl alcohol, and deionizer (DI) water. Then, a 6-µm layer of positive photo resist (AZ4620) was spin-coated, soft baked, and patterned. Cr, Ni, and Au (20, 80, 350 nm) were evaporated and lifted off in acetone to create contacts for solder coating, an adhesion layer for the electroplated antenna, and low resistance connections from the chip to the sensor. After lift-off, SU-8 was deposited to restrict solder wetting. Next, a 40-nm seed layer of Au was deposited over the wafer, AZ4620 was used to pattern the antenna, and 5 µm of Au was plated to reduce the antenna ohmic loss (improve the antenna efficiency). The seed layer was etched using Gold Etch TFA (Transene) mixed with DI water in a ratio of 5:1 (vol/vol). Then, a 25-µm layer of SU-8 was used to mask the metal features and create an opening for the sensor. The wafer was dried with nitrogen gas, and then individual contact lenses with 1 cm in diameter were cut out using a $CO_2$ laser cutter.

The aluminum IC pads were nickel/gold plated using an electroless technique (CVinc.). Then, the chip and exposed solder pads on the contact lens were coated with a low melting temperature solder. To accomplish this, indium-based solder (Indium Corporation, Indalloy 19, 60° C.) was heated in a beaker while covered by 10-mL ethylene glycol (EG) and 60-µL HCl. After the solder had melted completely, a pipette was used to solder coat all exposed pads on the IC and contact lens. The chip was then roughly aligned over the contact lens using tweezers in a petri dish of 25 mL of EG and 10-µL HCl. The petri dish was heated on a hotplate until the solder reflowed, and the chip was aligned by solder capillary forces. The lens can be molded with heat and pressure to the curvature of the eye and then Parylene can be deposited (except the sensing area) for biocompatible encapsulation.

Performance

Figure 27:
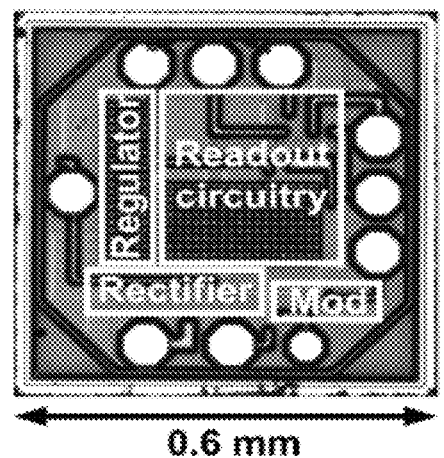
FIG. 27: Micrograph of readout IC.

The chip was implemented in a 0.13-µm CMOS process. FIG. 27 shows a micrograph of the readout IC. The chip area is 0.6×0.6 $mm^2$. A ground shield made of the 4-µm-thick top aluminum metal covers the sensitive regulator and readout circuitry to reduce the impact of EMI and light sensitivity.

Figure 28:
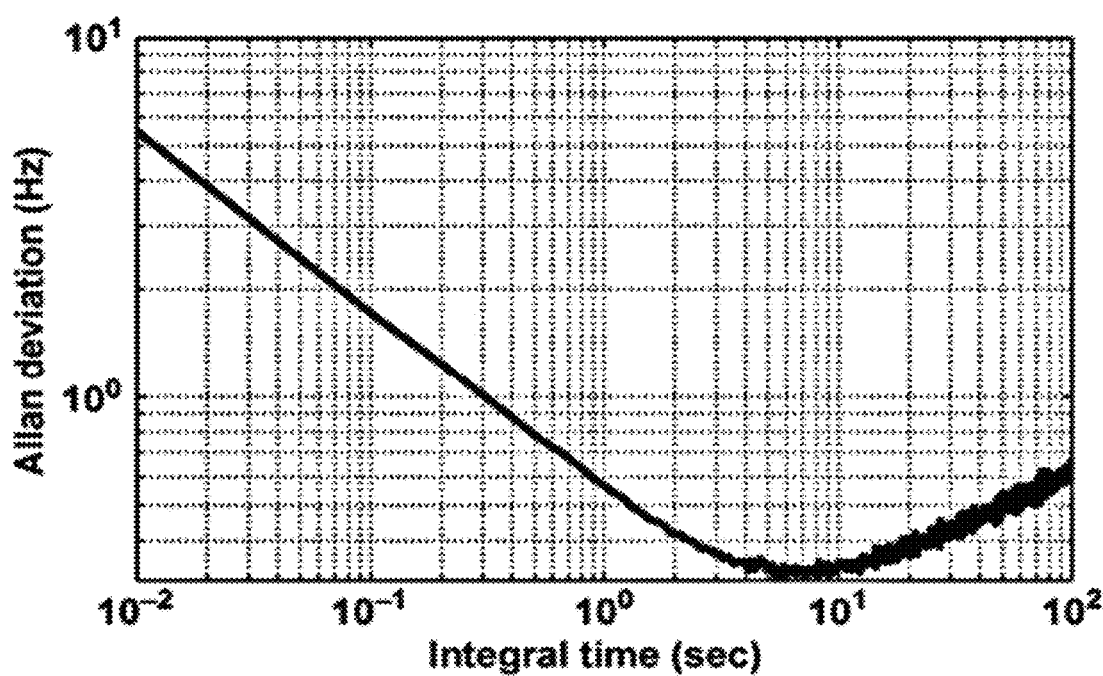
FIG. 28: Allan deviation plot of readout circuits after divider (center frequency=850 Hz).
Figure 29:
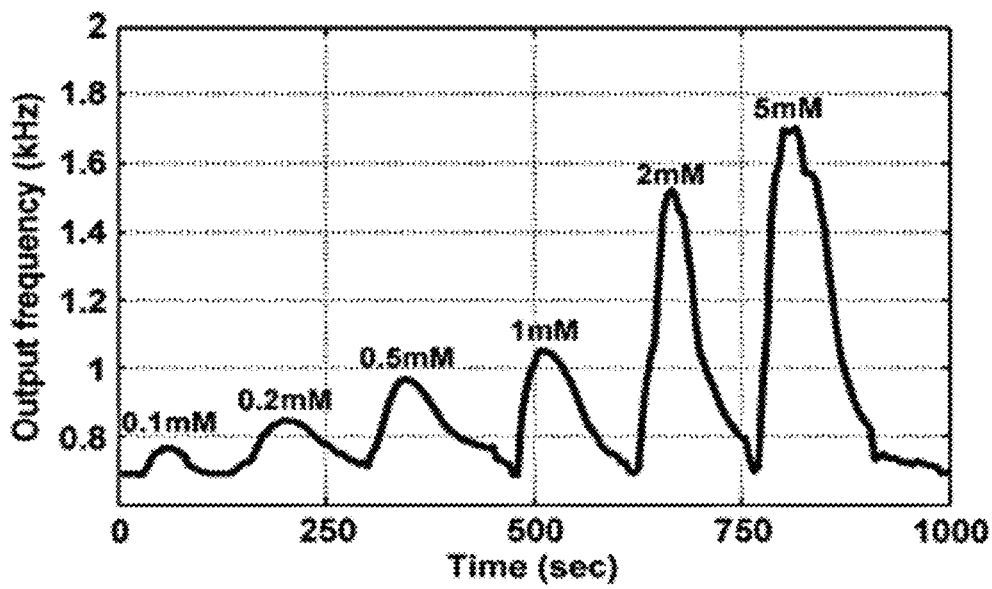
FIG. 29: Measured output response of readout IC (continuous glucose flow test).
Figure 30:
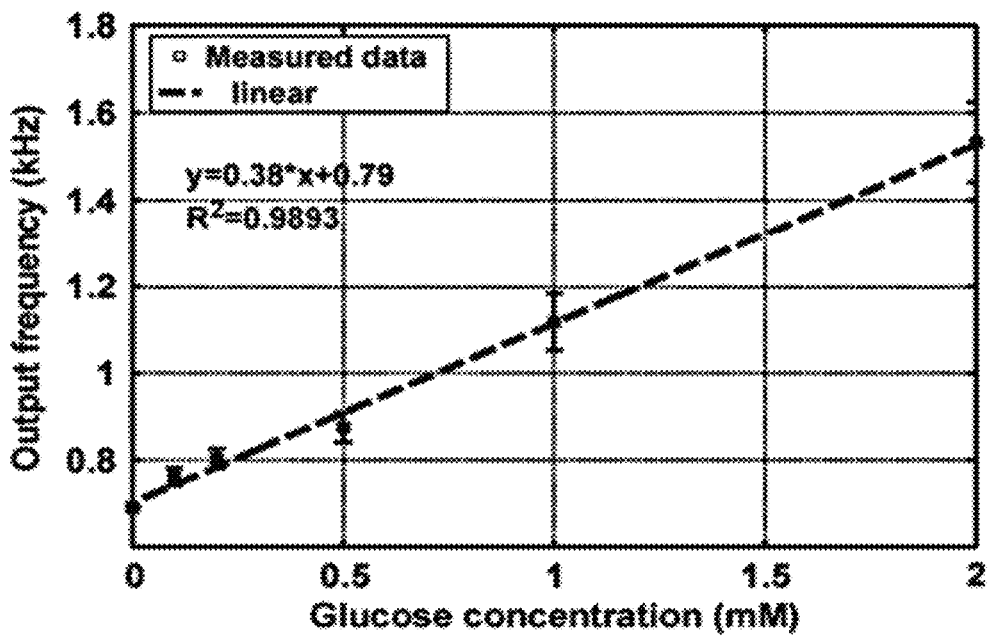
FIG. 30: Measured output frequency versus glucose concentration.
Figure 31:
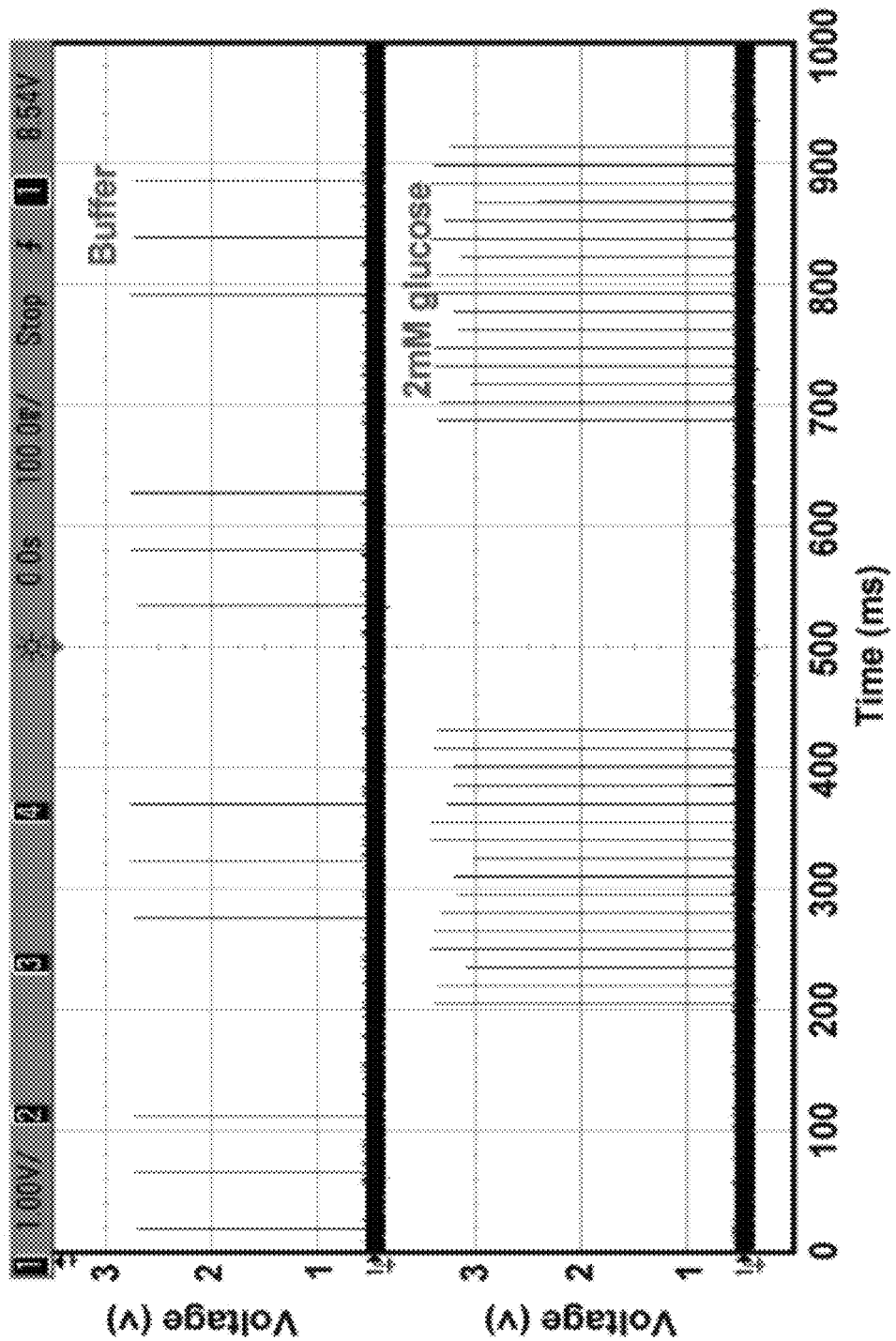
FIG. 31: Measured of LED driver outputs versus glucose levels.

The chip and sensor are first assembled on a PCB to characterize functionality and performance. The measured Allan deviation (over 6 h) of the readout circuitry is shown in FIG. 28. A minimum standard deviation of 0.31 Hz (center frequency of 850 Hz) is achieved while data are sampled at a period of 5 seconds. The measured results of a continuous glucose flow test (FIG. 16) are shown in FIG. 29. A buffer solution was added after each concentration to flush out the remaining ions of previous solutions. The output was sampled every 5 s to achieve a low noise floor, corresponding to the minimal Allan deviation. FIG. 17 shows the measured modulation frequency versus glucose concentration. The measured gain of the glucose sensor is 400 Hz/mM with a linear correlation (R-square) of 0.98 in 20 measurements from two different sensor assemblies. The resulting noise floor of readout circuitry is 0.775 μM (0.31 Hz/400 Hz/mM). FIG. 31 shows the measured outputs of LED driver with a buffer solution and glucose concentration of 2 mM. Each pulse above the baseline (3) for buffer solution represents a glucose level increase of ~0.15 mM.

Figure 32:
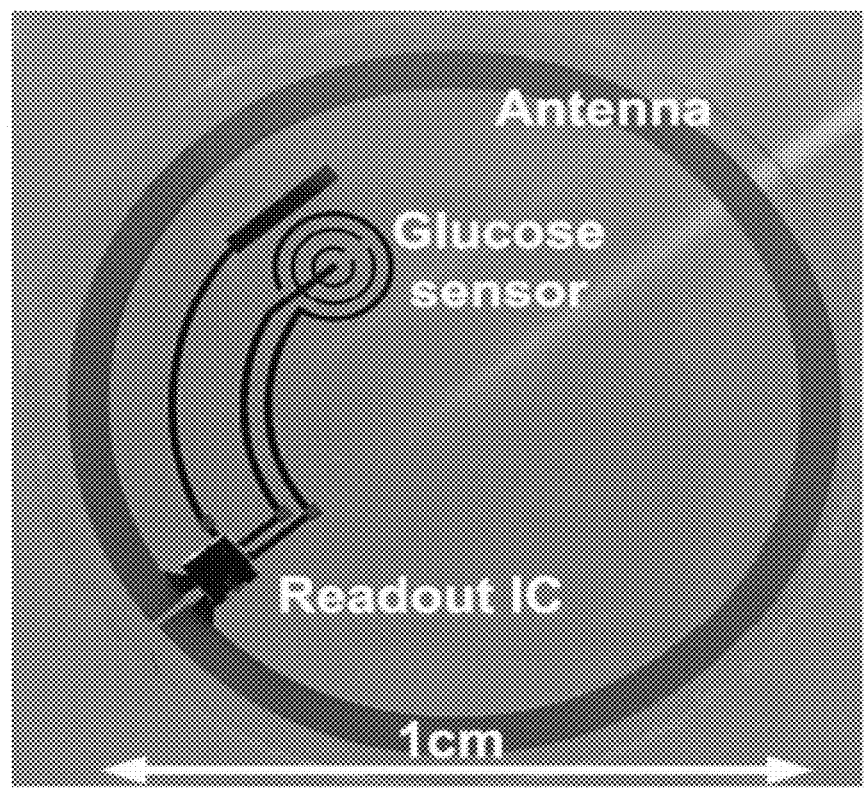
FIG. 32: Photograph of the assembled lens.
Figure 33A:
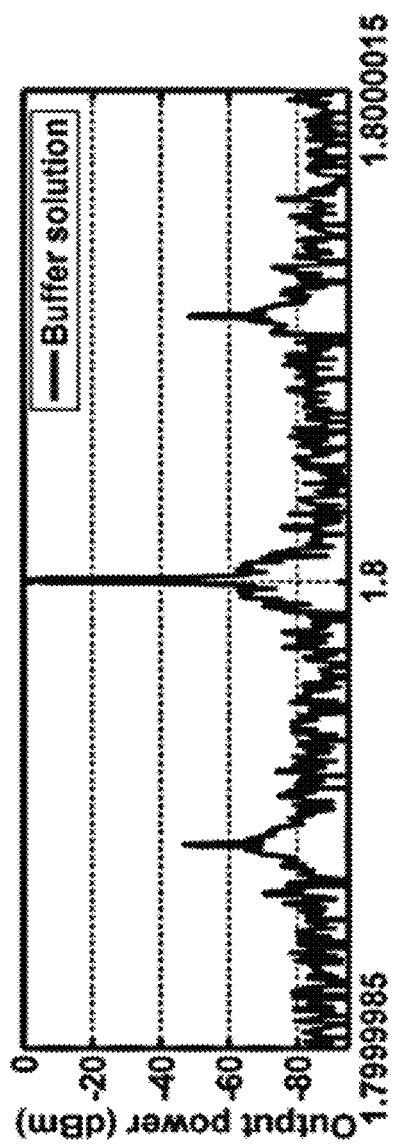
FIGS. 33A and 33B: Measured wireless transmission results (RF backscattering) of an assembled lens.
Figure 33B:
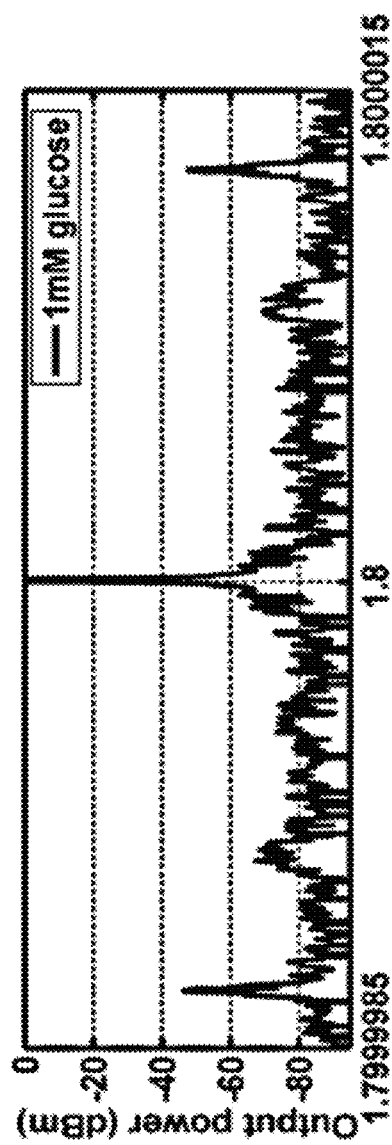

We assembled a loop antenna, a readout IC, and glucose sensor on a PET substrate, shown in FIG. 32. The chip is first gold-plated and flip-chipped on the substrate to reduce the contact resistance and bond wire inductance. The glucose sensor system consumes 3 μW, which gives a power link budget in the design and can be powered over 15 cm from an effective isotropic ally radiated power (EIRP) of 40 dBm at 1.8 GHz. This power level complies with the IEEE C95 standard, which regulates a maximum power density of 6 mW/cm$^2$ at 1.8 GHz for human exposure to an RF electromagnetic field, requiring a safety distance of at least 11 cm from an EIRP of 40-dBm power source. The transmitted RF power can be reduced by improving impedance matching, reducing antenna loss, and exploiting different rectifier designs.

FIG. 32 shows the measured backscattered signal from the assembled lens. The glucose concentration of 1 mM results in a 400-Hz frequency deviation of the backscattering carrier. Table 1 is the performance summary of our CMOS glucose sensor.

TABLE 1

PERFORMANCE SUMMARY

| | This work | M. Ahmadi and G. Jullien[1] | M. R. Haider, et al.[2] |
|---|---|---|---|
| Modulation scheme | FM-LSK | FM-LSK | ASK/FSK |
| Carrier frequency | 1.8 GHz | 13.56 MHz | 924 kHz |
| Sensor performance | | | |
| Glucose level | 0.05-1 mM (tear) | 0-40 mM (blood) | N/A |
| Sensing area | 0.22 mm$^2$ | 4.2 mm$^2$ | N/A |
| Glucose sensitivity | 0.18 μA · mm$^{-2}$ · mM$^{-1}$ | N/A | N/A |
| Readout circuitry performance | | | |
| Power consumption | 3 μW (measured) Regulator + bandgap reference: 1 μW (simulated) Ring oscillator × 2: 600 nW (simulated) Potentiostat: 500 nW (simulated) Digital blocks: 400 nW (simulated) | 110 μW | 400 μW/1.67 mW |
| Full scale measured current | 150 nA | 1 μA | 2 μA |
| Wirelessly-readout distance | 15 cm (in the air) | 4 cm | N/A |
| Sensitivity | 400 Hz/mM | N/A | 4.7 kHz/μA |
| Noise Floor | 0.775 μM | N/A | 3.93 fA/√(Hz) |
| Temperature stability | 20 Hz/° C. 2.6 Hz/° C. (differential measurement) | N/A | N/A |
| Chip size | 0.36 mm$^2$ | 1.69 mm$^2$ | 0.66/2.25 mm$^2$ |
| Energy storage capacitor | on-chip | on-chip | external power supply |

[1] M. Ahmadi and G. Jullien, "A wireless-implantable microsystem for continuous blood glucose monitoring," *IEEE Trans. Biomed. Circuits Syst.* 3(3): 169-180, June 2009.
[2] M. R. Haider, et al. "Low-power low-voltage current read-out circuit for inductively-powered implant system," *IEEE Trans. Biomed. Circuits Syst.* 4(4): 205-213, 2010

While illustrative embodiments have been illustrated and described, it will be appreciated that various changes can be made therein without departing from the spirit and scope of the invention.

The embodiments of the invention in which an exclusive property or privilege is claimed are defined as follows:

1. A powered contact lens formed from a transparent substrate shaped to be worn directly over a user's eye, the contact lens comprising:
   (a) an annular antenna disposed at a margin of the contact lens, wherein the antenna is configured to both receive a power signal and transmit a data signal;
   (b) a biosensor module configured to measure a characteristic of the user's eye, the biosensor module comprising an electromechanical sensor comprising:
      (i) a working electrode;
      (ii) a counter electrode;
      (iii) a reference electrode; and
      (iv) a biosensor circuit configured to measure the voltage of the working electrode, the counter electrode, and the reference electrode, and to transmit a biosensor signal;

wherein the working electrode, the counter electrode, and the reference electrode are all configured to be in electronic communication when the contact lens is worn on the user's eye; and (c) a communications module configured to:
(i) process the power signal from the antenna to provide operational power to the biosensor module; and
(ii) process the biosensor signal to provide the data signal to the antenna.

2. The contact lens of claim 1, wherein the counter electrode is annular in shape.

3. The contact lens of claim 1, wherein the working electrode comprises a plurality of concentric rings in electronic communication.

4. The contact lens of claim 1, wherein the working electrode comprises a plurality of concentric rings in electronic communication, and wherein the counter electrode is a concentric ring surrounding the working electrode.

5. The contact lens of claim 1, wherein at least one of the working electrode, the counter electrode, and the reference electrode comprises a metal stack of palladium intermediate titanium and platinum, wherein the stack is configured such that platinum is facing the user's eye.

6. The contact lens of claim 1, wherein the communication module and the antenna are configured to transmit the data signal using backscatter modulation.

7. A powered contact lens formed from a transparent substrate shaped to be worn directly over a user's eye, the contact lens comprising:

(a) an annular antenna disposed at a margin of the contact lens, wherein the antenna is configured to receive a power signal;
(b) a light-emitting diode (LED) configured to transmit a data signal;
(c) a biosensor module configured to measure a characteristic of the user's eye, the biosensor module comprising an electromechanical sensor comprising:
    (i) a working electrode;
    (ii) a counter electrode;
    (iii) a reference electrode; and
    (iv) a biosensor circuit configured to measure the voltage of the working electrode, the counter electrode, and the reference electrode, and to transmit a biosensor signal;

wherein the working electrode, the counter electrode, and the reference electrode are all configured to be in electronic communication when the contact lens is worn on the user's eye; and (d) a communications module configured to:
(i) process the power signal from the antenna to provide operational power to the biosensor module; and
(ii) process the biosensor signal to provide the data signal to the LED.

8. A powered contact lens formed from a transparent substrate shaped to be worn directly over a user's eye, the contact lens comprising:

(a) a photovoltaic device disposed at a margin of the contact lens, wherein the photovoltaic device is configured to provide a power signal to the contact lens when exposed to electromagnetic radiation;
(b) a light-emitting diode (LED) configured to transmit a data signal;
(c) a biosensor module configured to measure a characteristic of the user's eye, the biosensor module comprising an electromechanical sensor comprising:
    (i) a working electrode;
    (ii) a counter electrode;
    (iii) a reference electrode; and
    (iv) a biosensor circuit configured to measure the voltage of the working electrode, the counter electrode, and the reference electrode, and to transmit a biosensor signal;

wherein the working electrode, the counter electrode, and the reference electrode are all configured to be in electronic communication when the contact lens is worn on the user's eye; and (d) a communications module configured to:
(i) process the power signal from the photovoltaic device to provide operational power to the biosensor module; and
(ii) process the biosensor signal to provide the data signal to the LED.

9. The powered contact lens of claim 1, wherein the characteristic of the user's eye is a glucose level.

10. The powered contact lens of claim 7, wherein the characteristic of the user's eye is a glucose level.

11. The powered contact lens of claim 8, wherein the characteristic of the user's eye is a glucose level.

* * * * *

UNITED STATES PATENT AND TRADEMARK OFFICE
CERTIFICATE OF CORRECTION

PATENT NO. : 8,608,310 B2
APPLICATION NO. : 13/401569
DATED : December 17, 2013
INVENTOR(S) : B. Otis et al.

Page 1 of 1

It is certified that error appears in the above-identified patent and that said Letters Patent is hereby corrected as shown below:

In the Claims:

| COLUMN | LINE | ERROR |
|---|---|---|
| 32 (Claim 1, | 59 line 9) | "electromechanical" should read --electrochemical-- |
| 33 (Claim 7, | 38 line 11) | "electromechanical" should read --electrochemical-- |
| 34 (Claim 8, | 20 line 12) | "electromechanical" should read --electrochemical-- |

Signed and Sealed this
First Day of July, 2014

Michelle K. Lee
*Deputy Director of the United States Patent and Trademark Office*